(12) United States Patent
Emerson

(10) Patent No.: US 11,166,875 B2
(45) Date of Patent: Nov. 9, 2021

(54) TRANSFER DEVICE

(71) Applicants: THE REGENTS OF THE UNIVERSITY OF CALIFORNIA, Oakland, CA (US); THE UNIVERSITY OF SOUTHERN CALIFORNIA, Los Angeles, CA (US)

(72) Inventor: Jane F. Emerson, Irvine, CA (US)

(73) Assignee: The Regents of The University of California, Oakland, CA (US)

( * ) Notice: Subject to any disclaimer, the term of this patent is extended or adjusted under 35 U.S.C. 154(b) by 1128 days.

(21) Appl. No.: 15/545,601

(22) PCT Filed: Jan. 22, 2016

(86) PCT No.: PCT/US2016/014537
§ 371 (c)(1),
(2) Date: Mar. 28, 2018

(87) PCT Pub. No.: WO2016/153590
PCT Pub. Date: Sep. 29, 2016

(65) Prior Publication Data
US 2018/0296748 A1    Oct. 18, 2018

Related U.S. Application Data

(60) Provisional application No. 62/237,407, filed on Oct. 5, 2015.

(30) Foreign Application Priority Data

Jan. 22, 2015 (EP) ..................................... 15152110

(51) Int. Cl.
*A61J 1/20* (2006.01)
*A61M 5/32* (2006.01)
(Continued)

(52) U.S. Cl.
CPC ............. *A61J 1/2017* (2015.05); *A61J 1/201* (2015.05); *A61J 1/2013* (2015.05); *A61J 1/2051* (2015.05);
(Continued)

(58) Field of Classification Search
CPC ........ A61J 1/201; A61J 1/2013; A61J 1/2017; A61J 1/2096; A61J 1/2072; A61J 1/2089;
(Continued)

(56) References Cited

U.S. PATENT DOCUMENTS 5,329,976 A    7/1994  Haber
6,596,180 B2   7/2003  Baugh et al.
(Continued)

FOREIGN PATENT DOCUMENTS

JP    2000342557    12/2000
JP    2013522186    6/2013
(Continued)

OTHER PUBLICATIONS

International Search Report for PCT/US2016/014537 filed Jan. 22, 2016 the International search report dated Sep. 12, 2017.

*Primary Examiner* — John Kim
(74) *Attorney, Agent, or Firm* — Fish IP Law, LLP

(57) ABSTRACT

Compositions and methods for separating a sample of whole blood or bone marrow aspirate into a fraction rich in at least one of platelets and pluripotent cells are provided. A sample of whole blood can be centrifuged in a collection tube comprising a separator substance formulated to settle between the PRP fraction and the at least one other fraction. Preferably, centrifugation is completed without substantial activation of platelets. Optionally, the separator substance could be hardened to form a solid barrier that allows removal of all or substantially all of the platelets in the PRP fraction without remixing of the PRP fraction with the at least one (Continued)

other fraction. Transfer devices and methods are also provided in which a sterile sample can be transferred from a separation/preparation container (e.g., vacutainer) to a consumer or other container (e.g., dropper) while maintaining sterility of the sample.

11 Claims, 17 Drawing Sheets

(51) Int. Cl.
    *A61M 1/00*     (2006.01)
    *B04B 5/04*     (2006.01)
    *B01L 3/00*     (2006.01)

(52) U.S. Cl.
    CPC ........... *A61J 1/2058* (2015.05); *A61J 1/2065* (2015.05); *A61J 1/2068* (2015.05); *A61J 1/2072* (2015.05); *A61J 1/2075* (2015.05); *A61J 1/2089* (2013.01); *A61J 1/2096* (2013.01); *A61M 1/00* (2013.01); *A61M 5/32* (2013.01); *A61M 5/3202* (2013.01); *B04B 5/0414* (2013.01); *A61M 2202/0415* (2013.01); *A61M 2202/0427* (2013.01); *A61M 2202/10* (2013.01); *B01L 3/50215* (2013.01); *B01L 3/56* (2013.01); *B01L 2200/0647* (2013.01); *B01L 2200/0684* (2013.01); *B01L 2300/045* (2013.01); *B01L 2300/0672* (2013.01); *B01L 2300/0832* (2013.01)

(58) Field of Classification Search
    CPC ...... A61J 1/2065; A61J 1/2058; A61J 1/2068; A61J 1/2075; A61J 1/2051; B04B 5/0414; B01L 3/50215; B01L 3/56; B01L 2200/0647; B01L 2200/0684; B01L 2300/0832; B01L 2300/0672; B01L 2300/045; A61M 5/32; A61M 5/3202; A61M 1/00; A61M 1/029; A61M 1/3693; A61M 2202/0415; A61M 2202/10; A61M 2202/0427

See application file for complete search history.

(56) References Cited

U.S. PATENT DOCUMENTS

| | | |
|---|---|---|
| 6,610,002 B2 | 8/2003 | Dolecek |
| 6,827,863 B2 | 12/2004 | Dolecek et al. |
| 6,899,813 B2 | 5/2005 | Dolecek et al. |
| 7,673,758 B2 | 3/2010 | Emerson |
| 7,674,388 B2 | 3/2010 | Emerson |
| 7,775,962 B2 | 8/2010 | Emerson |
| 7,780,861 B2 | 8/2010 | Emerson |
| 7,971,730 B2 | 7/2011 | Emerson |
| 8,151,996 B2 | 4/2012 | Emerson |
| 8,206,638 B2 | 6/2012 | Emerson |
| 8,282,540 B2 | 10/2012 | Emerson |
| 8,318,077 B2 | 11/2012 | Emerson |
| 2001/0055621 A1 | 12/2001 | Baugh et al. |
| 2002/0068896 A1* | 6/2002 | Robinson ............... A61J 1/2089 604/82 |
| 2003/0144633 A1* | 7/2003 | Kirchhofer ........... A61M 5/326 604/201 |
| 2006/0184103 A1 | 8/2006 | Paproski |
| 2009/0294383 A1 | 12/2009 | Dolecek et al. |
| 2011/0168294 A1 | 7/2011 | Jakobsen |
| 2012/0078214 A1 | 3/2012 | Finke |
| 2012/0192976 A1* | 8/2012 | Rahimy ............... A61J 1/2089 137/798 |
| 2014/0113795 A1 | 4/2014 | Emerson |

FOREIGN PATENT DOCUMENTS

| | | |
|---|---|---|
| JP | 2014506319 | 3/2014 |
| WO | 2010077534 | 7/2010 |
| WO | 2014120797 | 8/2014 |
| WO | 0208007 | 1/2021 |

* cited by examiner

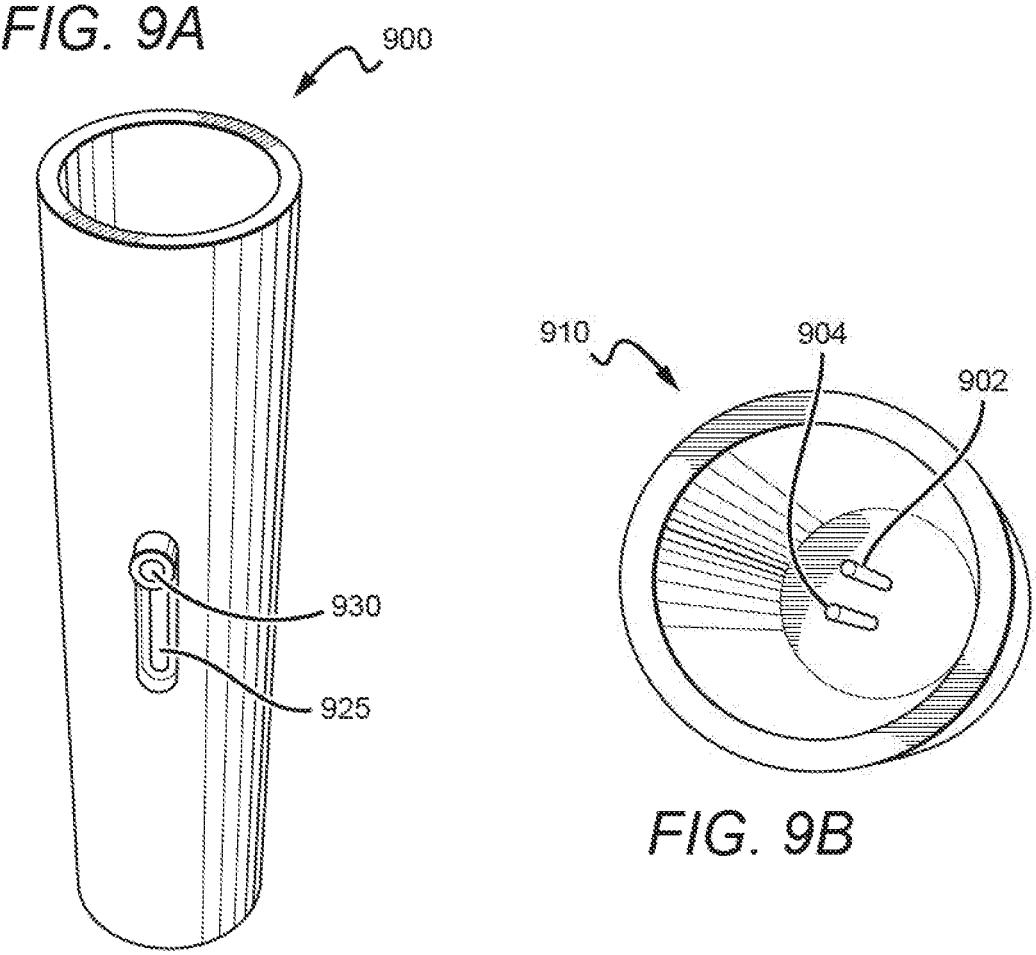
FIG. 9A
FIG. 9B
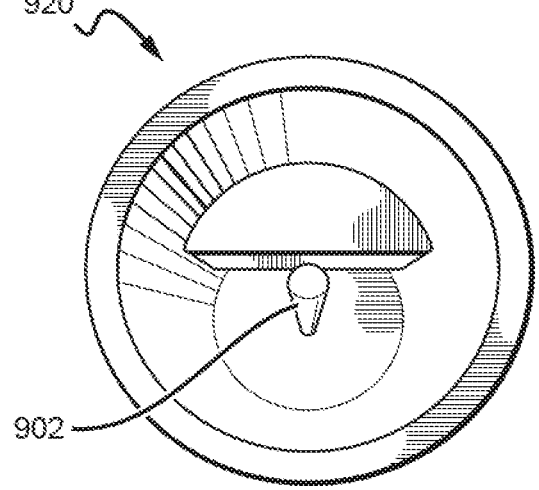
FIG. 9C

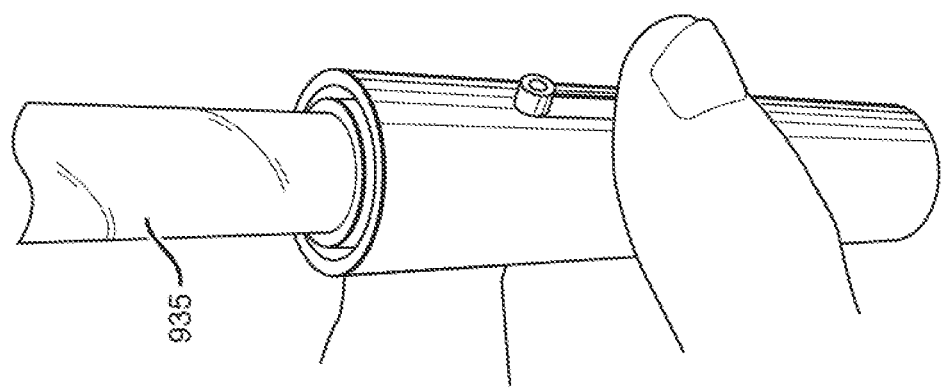
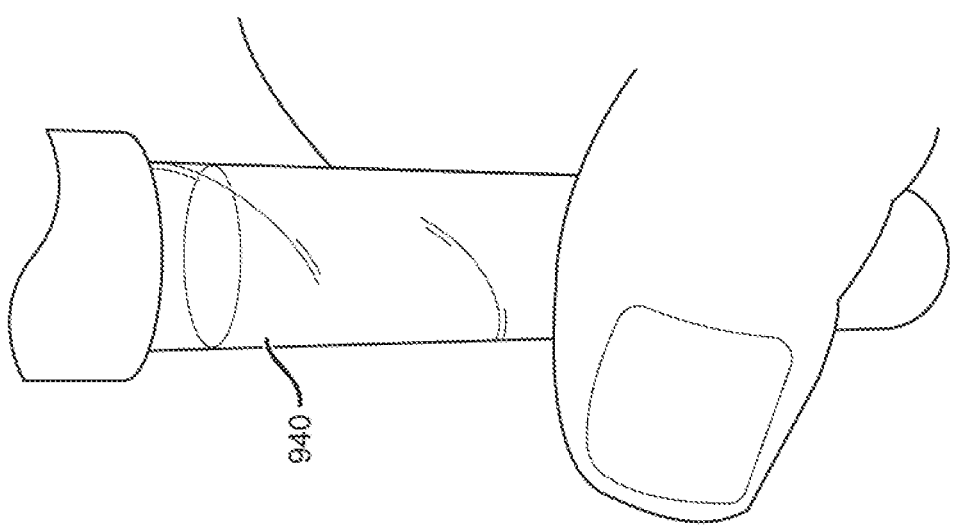
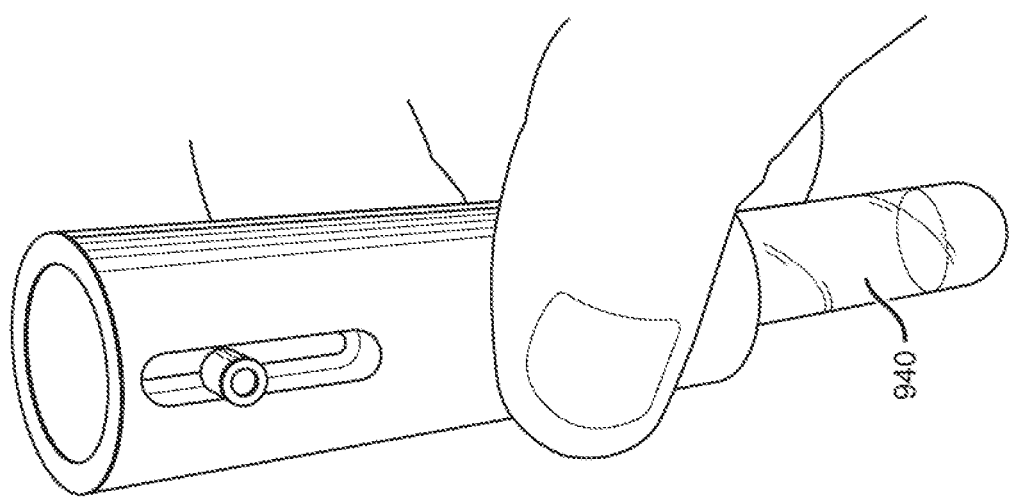

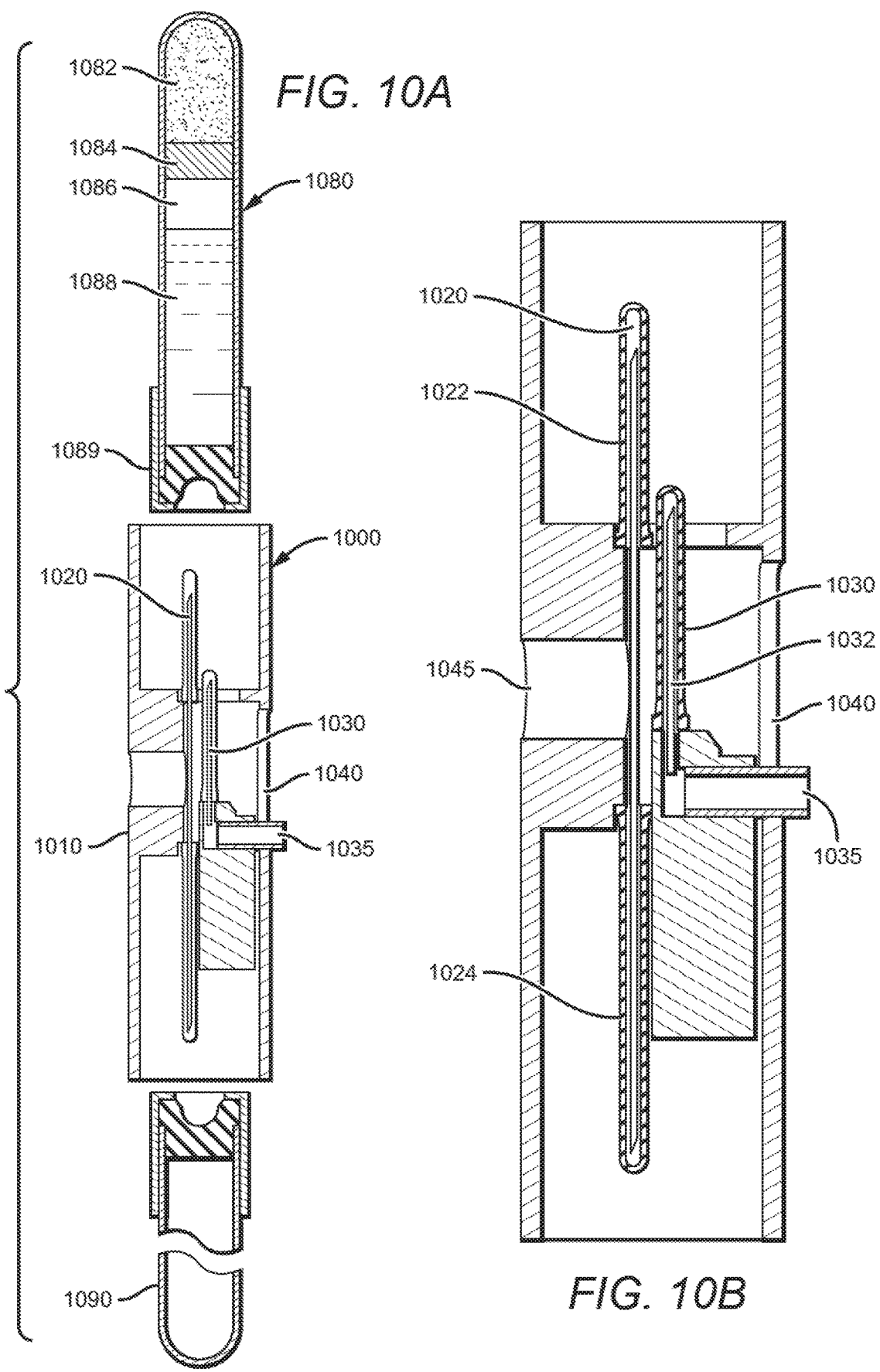

TRANSFER DEVICE

This application claims priority to PCT/US16/14537, filed Jan. 22, 2016, European Patent Application serial number 15152110.1, filed Jan. 22, 2015, and to U.S. Provisional Application Ser. No. 62/237,407, filed Oct. 5, 2015. These and all other extrinsic references are incorporated herein by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is separation technologies.

BACKGROUND

The background description includes information that may be useful in understanding the present invention. It is not an admission that any of the information provided herein is prior art or relevant to the presently claimed invention, or that any publication specifically or implicitly referenced is prior art.

Platelet-Rich Plasma (PRP) therapy has been used for bone repair and regeneration, plastic surgery, oral surgery applications and eye treatment, and is receiving increased attention and recognition for its effectiveness in treating sports injuries, nerve injuries, tendonitis and osteoarthritis. PRP can be viewed as a concentrated source of platelets that can be delivered to the site of an injury, and activated to allow for rapid growth factor release and stimulation of bone or soft tissue recovery. Early unintentional activation of platelets should be avoided as many growth factors have short half-lives and greater effectiveness can result if they are activated at or just prior to use (e.g., injection).

Some effort has been set forth in preparing or separating PRP using centrifugation methods. Examples include U.S. Pat. Nos. 6,596,180, 6,610,002, 6,827,863, 6,899,813, U.S. Patent Application Publication No. 2009/0294383, and International Patent Application Publication No. WO 02/081007. Unfortunately, known methods suffer at least one of several disadvantages, including high platelet activation, inability to remove all or substantially all of the PRP without risking aliquoting a buffy coat or gel with the PRP, or inability to obtain homogeneity of the PRP and the requirement for sterile open tube processing.

"Platelet Separation From Whole Blood in an Aqueous Two-Phase System With Water-Soluble Polymers" by Sumida et al. published in J Pharmacol Sci 101, 91-97 (2006) recognized a problem of high platelet activation using conventional centrifugation methods, and developed a method to separate platelets without centrifugation. More specifically, various polymers were mixed with whole blood containing citrate dextrose and observed blood cell separation and platelet activation. Unfortunately, Sumida found that where polymers separated platelets more efficiently, more platelets were activated. Conversely, where decreased activation of platelets was achieved, there was a poor platelet yield. In addition, because of sedimentation protocols, platelets are typically not homogenously distributed in PRP fractions, and quantification is therefore difficult.

Bone marrow aspirates containing regenerative pluripotent stem cells have also been used to help treat various bone and joint conditions. Unfortunately, known centrifugation methods cause significant loss of desired cells (e.g., B-cells, platelets, T-cells, monocytes, hematopoietic stem cells, mesenchymal stromal cells, endothelial progenitor cells, small embryonic-like cells).

Thus, there is still a need for improved methods of preparing PRP and bone marrow aspirate fractions.

Still further, prior separation efforts apparently require pipetting or manually removing a PRP or bone marrow aspirate fraction (or other fraction of a fluid) from the collection tube in which it is prepared or separated for transfer into a separate storage container for commercial uses. The removal step can have one or more undesired effects, including for example, not aliquoting all of the PRP or other desired fraction, breaking sterility, aliquoting unwanted fractions or materials, or contamination.

Thus, there is still a need in the art for improved sterile transfer devices and methods.

SUMMARY OF THE INVENTION

The inventive subject matter provides apparatuses, systems and methods in which a platelet-rich plasma (PRP) fraction having a desired concentration of functioning platelets is separated from a sample of whole blood. The inventive subject matter also provides apparatuses, systems and methods in which a bone marrow aspirate fraction (BMAF) having a desired concentration of functioning platelets or other cells is separated from a sample of bone marrow fluid. The separation is achieved using a polymerizable separator substance that is flowable with whole blood and curable to form a solid barrier.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, a PRP fraction comprises at least 150% of the platelet concentration in the sample of whole blood, less than 20% of the white blood cells from the sample of whole blood it is obtained from, and less than 20% of the red blood cells from the sample of whole blood it is obtained from. It should be appreciated that platelet, WBC and RBC levels could be determined pre-separation and post-separation via a complete blood count (CBC), blood smear, or any other commercially suitable test.

As used herein, a bone marrow aspirate fraction (BMAF) comprises at least 100% of the viable platelet concentration in the bone marrow aspirate pre-centrifugation. In some preferred embodiments, the BMAF can comprise at least 105%, at least 110%, at least 115%, at least 120%, at least 125% or even more of the viable platelet concentration in the bone marrow aspirate pre-centrifugation. Platelet recovery from bone marrow aspirates has been much more variable than platelet recovery from whole blood samples. Applicant surprisingly discovered that centrifugation of bone marrow aspirates using polymerizable separator substances of the inventive subject matter yielded a platelet rich fraction with greater viable platelet concentrations compared to known systems, and less cell damage or death. As centrifugation of bone marrow aspirates separates platelets and stem cells from the bone marrow sample, it is expected that the increase in viable platelet concentrations correlates to greater stem cell separation/capture.

The polymerizable separator substance can be included in a collection tube with the sample of whole blood that is centrifuged until the polymerizable separator substance settles between the PRP fraction and a non-PRP fraction of the sample of whole blood. Since the polymerizable separator substance (prior to curing) comprises smaller building blocks (e.g., oligomers), substantially less friction and shear forces result between the platelets (or other desired cells) and the separator substance materials, resulting in lower activation of platelets and lower cell death or damage.

Once the polymerizable separator substance settles between the PRP and non-PRP fractions (or other fractions of a fluid), the polymerizable separator substance can be hardened to form a solid barrier, wherein the polymerizable separator substance of the solid barrier has an average molecular weight that is higher than the average molecular weight of the polymerizable separator substance when flowable, and wherein the polymerization does not have a substantially adverse affect on platelet viability. The solid barrier will preferably be stationary with respect to the collection tube and impermeable to a degree that prevents mixing of the PRP fraction and the non-PRP fraction upon agitation. This will advantageously allow a user to homogenize the PRP fraction and entirely remove it from the collection tube without remixing the PRP and non-PRP fractions.

The present invention also provides apparatus, systems, and methods in which a sterile sample can be transferred from a separation/preparation container (e.g., vacutainer) to a consumer or other container (e.g., dropper) while maintaining sterility of the sample.

In one aspect of the inventive subject matter, a transfer device comprises a housing that encloses a base and at least two needles. The housing can comprise two open ends (e.g., a cylindrical tube), and include two internal sections on opposite sides of the enclosed base.

One of the two needles could be coupled to a first portion of the base structure such that a first end of the needle is positioned within one internal section and a second end of the needle is positioned within a second internal section. It should be appreciated that in some embodiments, the first end of the needle and the second end of the needle could compose two separate needles positioned near opposite ends of a through hole of the base structure.

The second needle could be coupled to a second portion of the base structure such that it is movable relative to the housing, one end is positioned within the first internal section (next to the first end of the first needle), and a second end is positioned within the base—not in the second internal section. Preferably, the second end is coupled at an angle to a vent structure that extends out a slot of the housing.

The transfer devices presented herein can advantageously allow a user to transfer a fluid from one tube to another without compromising sterility. Additionally or alternatively, the transfer devices can allow the entire PRP fraction (or BMAF or other desirable fraction) to be transferred without shaking, rotating or otherwise manipulating the tubes.

One or more filters may be incorporated into the device. For example, one or more filters can be coupled to the air vent, the transfer needle, or any other portion of the device. Contemplated filters can at least one of (a) prevent leakage (e.g., when the device is tilted), and (b) sterilize air entering the device (e.g., vent, vent needle) or the preparation tube. In some embodiments, a filter can comprise a hydrophobic membrane.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 9A-9I illustrate a transfer device being used to transfer a separated substance from a first container to a second container.

FIGS. 10A-10E provide cross-sectional views of a transfer device being used to transfer a separated substance from one container to another.

DETAILED DESCRIPTION

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

One should appreciate that the disclosed techniques provide many advantageous technical effects including increased platelet separation in the presence of a polymerizable separator substance (PSS) without substantial activation of the separated platelets. Additionally, the compositions and methods provided allow a user to invert a collection tube upon polymerization of the separator substance to mix the separated PRP fraction or BMAF, without remixing with the separated phases or the PSS, until a substantially homogeneous distribution of platelets is obtained. Additionally, the methods and devices provided allow for commercial use of a BMAF, PRP or other fraction of a fluid without removing the fraction from the collection tube in which it was prepared or separated for placement into a separate storage container.

Figure 1:
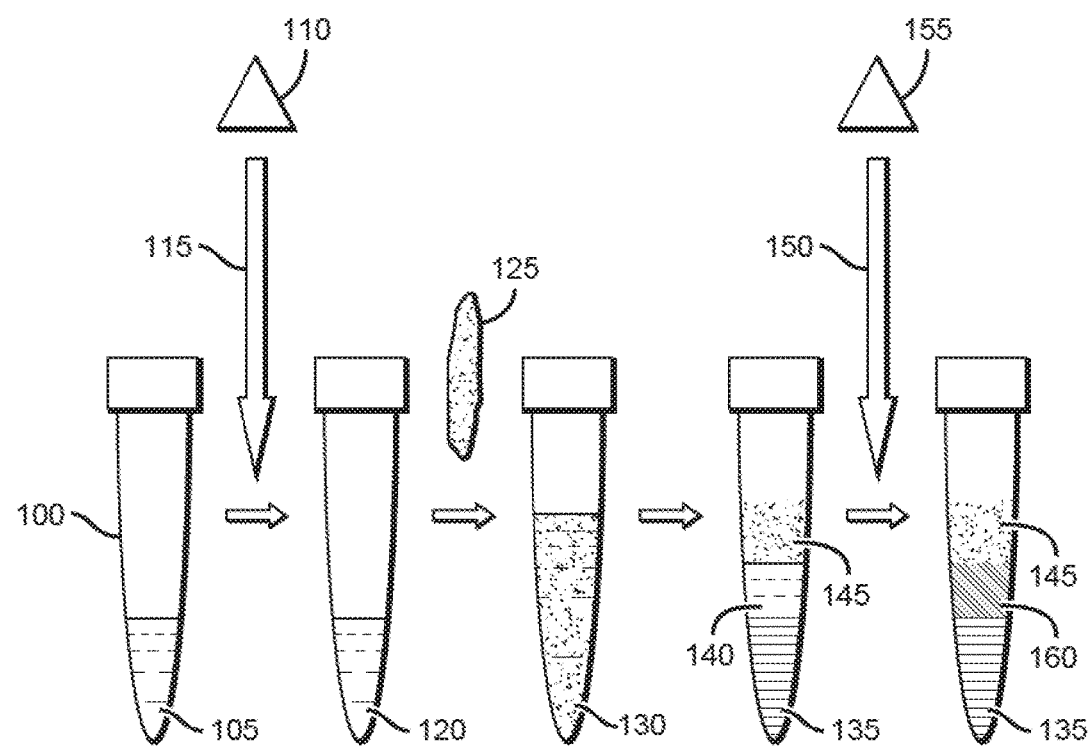
FIG. 1 illustrates a collection tube being used in accordance with a method of the inventive subject matter for separating a platelet rich plasma fraction of whole blood.

One embodiment of separating a PRP fraction in accordance with the inventive subject matter is schematically shown in FIG. 1. It is contemplated that any suitable collection tube could be used to perform methods of the inventive subject matter. The tube is preferably made of a rigid material (e.g., hard plastics, glass, etc.) suitable to support a vacuum within its lumen, and is of sufficient volume to hold a desirable sample of whole blood or bone marrow aspirate from which a desirable amount of PRP or BMAF can be separated. An exemplary tube includes the BD Vacutainer® products. Although the preferred devices and methods described herein include the use of a collection tube, it is contemplated that a collection tube could be replaced with other vessels such as flasks, jars, beakers, bottles or vials.

In the embodiment of FIG. 1, a collection tube 100 that contains a flowable/polymerizable separator substance 105 is exposed to a sterilizing energy source 110, which applies sterilization energy 115 (e.g., gamma radiation, e-beam radiation, heat) to the tube 100 and separator substance 105, resulting in a sterilized separation tube and sterilized (but still flowable and UV curable) separator substance 120. A sample of whole blood 125 can be added to tube 100, thereby forming a mixture 130 of the sample and sterilized separator substance.

The tube 100 and mixture 130 can then be centrifuged until the separator substance 140 component of the mixture 130 settles between a PRP fraction 145 and a non-PRP fraction 135 of the sample of whole blood 125. The PRP fraction 145 will preferably have a platelet concentration that is at least 150% the platelet concentration of the sample 125, and the non-PRP fraction 135 will preferably comprise at least 90% of the WBCs and RBCs from sample 125.

While the description herein is generally directed towards separation of a PRP fraction from a sample of whole blood, it should be appreciated that the same devices and methods could be used to separate a bone marrow aspirate fraction from bone marrow aspirates. In the collection tube, the BMAF would be positioned above the PSS, and the remaining components of the bone marrow aspirates would be positioned below the PSS.

Polymerizable separator substance 140 can be polymerizable in whole or in part. Therefore, exposure of the separator substance 140 to energy 150 (e.g., UV energy) generated by a suitable energy source 155 (e.g., UV light source) will initiate radical polymerization and cause at least a portion of the separator substance 140 to form a solid, crosslinked composition 160 that acts as an impermeable barrier between the PRP fraction 145 and the non-PRP fraction 135. In some embodiments, the final thickness of the barrier (after UV curing) will be no more than 10 mm, and more preferably no more than 5 mm.

The polymerizable separator substance (or the polymerizable portion of a polymerizable separator substance) could be formulated to polymerize within ten minutes to a hardness of at least 1 on the Shore 00 hardness scale, more preferably a hardness of at least 10 on the Shore A hardness scale, when triggered by a suitable energy source (e.g., UV light), and form a solid with respect to a probe, a pipette, decanting or even freezing. The hardened solid barrier formed can adhere to the walls of a lumen of a tube to substantially or completely seal the PRP fraction from one or more other fractions, thereby protecting the PRP fraction from contamination due to diffusion, agitation, sample extraction, or other undesirable interaction.

The suitable light source could emit a light having an intensity of between 5-100 W/cm$^2$, between 10-75 W/cm$^2$, between 15-50 W/cm$^2$, or any other suitable intensity—all measured at a distance of 10 cm from the light source. Additionally or alternatively, the suitable energy source could produce a light having a maximum peak at a wavelength of between 50-400 nm, for example between 200-280 nm (UVC), between 280-315 nm (UVB), between 315-400 nm (UVA), or between 200-400 nm. Additionally or alternatively, the suitable energy source could emit a light with a peak irradiance of between 0.1-10 W/cm$^2$, for example, between 0.3-1 W/cm$^2$, between 1.5-2.5 W/cm$^2$, or between 0.5-3.5 W/cm$^2$. Additionally or alternatively, the light produced by the suitable light source could arrive at the surface to be cured with a radiant energy density of between 0.3-8 J/cm$^2$, for example, between 1-5 J/cm$^2$, or between 1-2 J/cm$^2$.

One exemplary suitable light source is a custom light box made by Heraeus that produces a light having a maximum peak at a wavelength of 385 nm, and a peak irradiance of 2.2 W/cm$^2$. This light source was used with a power setting of 25% of maximum optical output power of 25 W. Some of the tested photocurable substances had a volume of between 0.25-1 mL, was disposed in vacutainer tubes, and the suitable energy sources were light emitting diodes emitting energy at between 380-390 nm, with a peak irradiance of 2.2 W/cm$^2$. However, it should be appreciated that one or more factors of exposure (e.g., irradiance, wavelengths, radiant energy) can be modified, concentrations of substance components could be modified (e.g., antioxidant concentration, photoinitiator concentration), or different energy sources could be used, to achieve a similar cure time for smaller or larger volumes.

Where a separator substance 140 is polymerizable only in part, it is contemplated that the non-polymerizable portion (e.g., a thixotropic gel component) can settle below the polymerizable portion such that the desired PRP fraction can be used or entirely removed from the collection tube without mixing of the PRP fraction with the non-PRP fraction or the non-polymerizable portion. The non-polymerizable portion could include, for example, off the shelf gels (e.g., BD Vacutainer® SST™, BD Vacutainer® PST™, Vacuette® blood collection tubes with gel separators, PPMA serum separator gel tubes, Polypropylene serum separator gel tubes, etc.), or any other commercially suitable gel.

It should be appreciated that a separator substance of the inventive subject matter, by virtue of the solid barrier formed, can allow a user to achieve and re-achieve substantial homogeneity of the BMAF, PRP or other fraction, for example, by mixing or otherwise agitating the PRP fraction in the collection tube without dislodging the barrier between the PRP and non-PRP fractions. Additionally, the substantial homogeneity could be achieved without disruption of the cells, for example, without substantial activation of the platelets. Additionally, where at least a portion of the separator substance is polymerizable to form a solid, curing the polymerizable separator substance can form a polymeric network that maintains separation of the PRP fraction as efficiently as, or even better than a polymeric separator substance would.

Some contemplated polymerizable separator substances can comprise: (1) an oligomer (e.g., a combination (e.g., Ebecryl, Cytec) thereof), with (2) a photoinitiator (e.g., Additol® BDK, Additol® TPO) and (3) a stabilizer (phenothiazine). Examples of contemplated photocurable compositions include, among other things, LAI (e.g., L1A1 and phenothiazine), and LAIR. As used herein, L=an oligomer (e.g., L1=Ebecryl 230 from Allnex, previously from Cytec Industries, Inc., etc.); A=a photoinitiator (e.g., A1=Additol BDK); I=a stabilizer (e.g., phenothiazine, etc.). See Table 1 below for more examples of components that may be included in a PSS.

TABLE 1

| ABBREVIATION | NAME |
| --- | --- |
| R | Gelling Agent (e.g., DBS, silica, etc.) |
| M | Monomer |
| M1 | Trimethylolpropane propoxylate triacrylate |
| L | Oligomer |
| L1 | Ebecryl 230 from Allnex |
| A | Photoinitiator |
| A1 | Additol BDK |
| I | Stabilizer |
| I1 | Phenothiazine |
| E | Antioxidant/radical scavenger (e.g., Vitamin E, BHT, BHA, carotene, bilirubin, ascorbic acid, etc.) |
| D | Density adjuster (e.g., Ebecryl 113 from Cytec, etc.) |
| T | Tempo nitroxide |

In some contemplated polymerizable separator substances, the photoinitiator (e.g., Azobisisobutyronitrile, Benzoyl peroxide, Camphorquinone, a phosphine oxide photoinitiator, a ketone-based photoinitiator, a benzoin ether photoinitiator) is present at a concentration of less than 10 wt %, less than 5 wt % or even less than 2 wt %, and a stabilizer is present at a concentration of less than 5 wt %, less than 2 wt %, less than 1 wt % or even less than 0.5 wt %. As a more specific, non-limiting example, a separator substance can comprise an oligomer present at a concentration of between 95 and 100% (e.g., 100 wt %), a photoinitiator present at a concentration of between 0.8 and 1.2% (e.g., 1 wt %), and a stabilizer present at a concentration of between 0.01 and 0.05% (e.g., 0.1 wt %).

Contemplated photoinitiators include, among other things, Additol BDK and Additol TPO. Contemplated stabilizers include, among other things, phenothiazine. A separator substance may also include an antioxidant, especially where irradiation sterilization of the collection tube with separator substance is desired without substantial curing of the separator substance. Irradiation sterilization may be preferred for high throughput, but the mechanism of action relies on free-radical generation which is inherently problematic due to unwanted premature curing of the separator substance. However, Applicant surprisingly found that where a radical scavenger such as tocopherol is included, some compositions of the inventive subject matter (e.g., LAIE) will maintain flowability during irradiation sterilization at a radiation dosage of more than 3 kG, while some other compositions (e.g., LAI) will not maintain flowability under the same radiation dosage as further discussed in application number PCT/US15/57359 and European application number 14190681.8, which are incorporated herein by reference. Viewed from another perspective, LAI was found to only maintain flowability during irradiation sterilization up to a radiation dosage of approximately 3 kG. In some preferred embodiments, the at least one of the radical scavenger and the antioxidant comprises tocopherol and is present in the composition in a molar concentration of at least 75 mM, more preferably at least 100 mM, and even more preferably at least 135 mM. Lower concentrations of tocopherol (e.g., less than about 75 mM) are not preferable for various reasons. For example, separator substances with lower tocopherol concentrations can only maintain flowability at lower radiation dosages, which may not allow for cost-effective sterilization under the ISO protocol. Additionally, separator substances with lower tocopherol concentrations typically require lower photoinitiator concentrations (e.g., less than 1 wt %), which generally requires a longer cure time.

Some contemplated antioxidants include hydroxyl containing (AOH) antioxidants (e.g., Vitamin E (α-tocopherol), Vitamin C (ascorbic acid), gallic acid), and Nitroxide (RNO) antioxidants (e.g., TEMPO (2,2,6,6-tetramethylpiperidine 1-oxyl), TEMPOL (4-Hydroxy-TEMPO). Viewed from another perspective, contemplated antioxidants include, among other things, tocopherol, butylated hydrozytoluene (BHT), butylated hydroxyanisole (BHA), carotene, bilirubin and ascorbic acid.

An exemplary polymerizable separator substance comprises an oligomer, a photoinitiator and a stabilizer, wherein the photoinitiator is present at a concentration of less than 5 wt % (e.g., between 0.1-5%, between 0.1-3%), and wherein the stabilizer is present at a concentration of less than 0.5 wt % (e.g., between 0.1-0.5%, between 0.1-0.3%).

LAI (e.g., L1, A1 and phenothiazine) composes some especially preferred photocurable compositions, and can be formulated to have the desired density range of 1.00-1.09 g/cm$^3$. Although experiments were conducted using a photocurable composition having an oligomer, it is contemplated that monomer-containing compositions may also be suitable for use in PRP preparation since many monomers and oligomers have similarly high reactivity, and many monomers and oligomers can polymerize in the presence of UV light.

Other examples of potentially suitable photocurable separator substances include those described in U.S. Pat. Nos. 7,674,388, 7,673,758, 7,775,962, 7,971730, 7,780,861, 8,206,638, 8,282,540, 8,151,996, and 8,318,077, LAIE (e.g., L1, A1, phenothiazine and tocopherol), and LAIER, wherein R=a gelling agent (e.g., DBS, silica, etc.), and E=at least one of an antioxidant and a radical scavenger (e.g., Vitamin E, butylated hydroxytoluene (BHT), butylated hydroxyanisole (BHA), carotene, bilirubin, ascorbic acid, etc.). While R and E are generally not necessary components of a photocurable composition, each can provide advantageous features to the photocurable composition for some uses. For example, a gelling agent may not be a necessary component of the photocurable composition where the separator substance also comprises a thixotropic soft gel component that is loaded into the collection tube above the photocurable composition such that no flow will result prior to use. Nonetheless, it may be desirable to have a thixotropic photocurable composition, for example, where it is desirable to have the sealant disposed in the tube without a soft gel component, or on top of the soft gel component. However, it should be noted that an increase in gelling agent concentration has been found to lead to premature curing during irradiation sterilization.

Still further examples are compositions including: (1) at least one of a monomer, and an oligomer (e.g., a combination (e.g., Ebecryl, Cytec) thereof), with (2) a photoinitiator (e.g., Additol® BDK, Additol® TPO) and (3) a stabilizer (phenothiazine). It should be appreciated that any commercially suitable photocurable compositions can be used. Suitable photocurable compositions are typically at least one of a gel (e.g., when a gelling agent is added (e.g., DBS or silica)) and flowable (with whole blood) prior to polymerization, and can solidify when exposed to a suitable energy source (e.g., UV light). These can include, among other things, MLA (e.g., M1L1A1), MLAI (e.g., M1L1A1 and phenothiazine), MAI (e.g., M1A1 and phenothiazine), LAI (e.g., L1A1 and phenothiazine), and LMA (e.g., L1M1A1).

As used herein, M=a monomer (e.g., M1, which is a monomer Trimethylolpropane propoxylate triacrylate from Sigma-Aldrich Cat. No. 407577); L=an oligomer (e.g., L1=Ebecryl 230 from Allnex, previously from Cytec Industries, Inc.); A=a photoinitiator (e.g., A1=Additol BDK); I=a stabilizer (e.g., phenothiazine).

A radical scavenger such as compounds having Vitamin E activity (e.g., tocopherol), while not necessary, can be included to allow the photocurable composition to be sterilized via irradiation without curing (e.g., by changing the density properties), rather than requiring heat sterilization to maintain a flowability effective to allow sedimentation between two fractions of a sample of whole blood. Where heat sterilization is desired, it can be achieved by exposing the collection tube and separator substance to a heat of at least 200 degrees Celsius, more preferably at least 225 degrees Celsius, and most preferably at least 250 degrees Celsius.

In some embodiments, where tocopherol or other suitable antioxidant is included, a collection tube including the separator substance can be sterilized to satisfy the International Organization for Standardization (ISO) protocols before being sold. Applicant surprisingly found that where a radical scavenger such as tocopherol is included, some compositions of the inventive subject matter (e.g., LAIE) will maintain flowability during irradiation sterilization at a radiation dosage of more than 3 kG, while some other compositions (e.g., LAI) will not maintain flowability under the same radiation dosage. Viewed from another perspective, LAI was found to only maintain flowability during irradiation sterilization up to a radiation dosage of approximately 3 kG. In some preferred embodiments, the at least one of the radical scavenger and the antioxidant comprises tocopherol and is present in the composition in a molar concentration of at least 75 mM, more preferably at least 100 mM, and even more preferably at least 135 mM. Lower concentrations of tocopherol (e.g., less than about 75 mM) are not preferable for various reasons. For example, separator substances with lower tocopherol concentrations can only maintain flowability at lower radiation dosages, which may not allow for cost-effective sterilization under the ISO protocol. Additionally, separator substances with lower tocopherol concentrations typically require lower photoinitiator concentrations (e.g., less than 1 wt %), which generally requires a longer cure time.

For example, tubes can be sterilized (preferably without substantial polymerization of the separator substance or portion thereof) using gamma radiation (e.g., from a Cobalt source (e.g., Colbalt 60)), using e-beam radiation (e.g., from a 7 MeV Pulsed Linear Accelerator (LINAC) Electron Beam source), gas (e.g., ethylene oxide), or a heat between 50-80 degrees Celsius for a duration of between about 10-60 minutes, or a heat between 100 to 250 degrees Celsius or even more. Viewed from another perspective, the separator substance can be effective to allow irradiation, gas, or heat sterilization without curing more than 40%, more preferably without curing more than 30%, and to allow subsequent polymerization via UV or other curing. An optional vacuum can be introduced, for example, by simply decompressing the volume of the tube's lumen by using a suitable pump.

All suitable sterilization times are contemplated (e.g., less than 10 minutes, less than 5 minutes, less than 2 minutes, between 5-120 seconds, between 5-90 seconds), where the collection tubes (and separator substances) are e-beam sterilized at dosages of between 5-25 kGy, more typically between 10-20 kGy. All suitable sterilization times are contemplated (e.g., less than 10 minutes, less than 5 minutes, less than 2 minutes, between 5-120 seconds, between 5-90 seconds), where the collection tubes (and separator substances) are gamma sterilized at dosages of between 5-25 kGy, more typically between 10-20 kGy. It has been observed that with gamma sterilization, weaker sources with lower dose delivery rates were more likely to cure the compound. The dose required by the ISO depends on, among other things, the bioburden of the object being sterilized. The radiation time required depends on not only the sterilization technique used, but also, for example, the bioburden of the object being sterilized, and the radiation dose (kGy).

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

It is also contemplated that a collection tube could be sterilized, and a sterilized separator substance could be subsequently added to the tube. Additionally or alternatively, a user could add one or more separator substances to a collection tube after purchase, as opposed to having a separator substance pre-disposed within the tube.

Where a sample (e.g., whole blood) is added to a collection tube of the inventive subject matter, centrifugation could separate the whole blood into a PRP fraction and a non-PRP fraction. When the separator substance has a density that is intermediate to that of the PRP and non-PRP fractions, it can migrate between the two fractions during centrifugation, thereby isolating the fractions from each other. The separator substance can then be rapidly hardened through polymerization when triggered by a suitable energy source to provide a solid barrier between the two fractions.

It is contemplated that an anticoagulant can be included in the collection tube, optionally as part of the separator substance, to prevent clotting of the sample of whole blood and obtain plasma containing fibrinogen and clotting factors. Contemplated anticoagulants include sodium citrate, EDTA, citrate dextrose, or any other suitable anticoagulant. It is noteworthy that even though radiation polymerization is initiated and performed, the chemistry used and especially acrylic polymerization will neither effect platelet activation or function, nor interfere with many or most other tests that can be performed on the PRP fraction.

Figure 2:
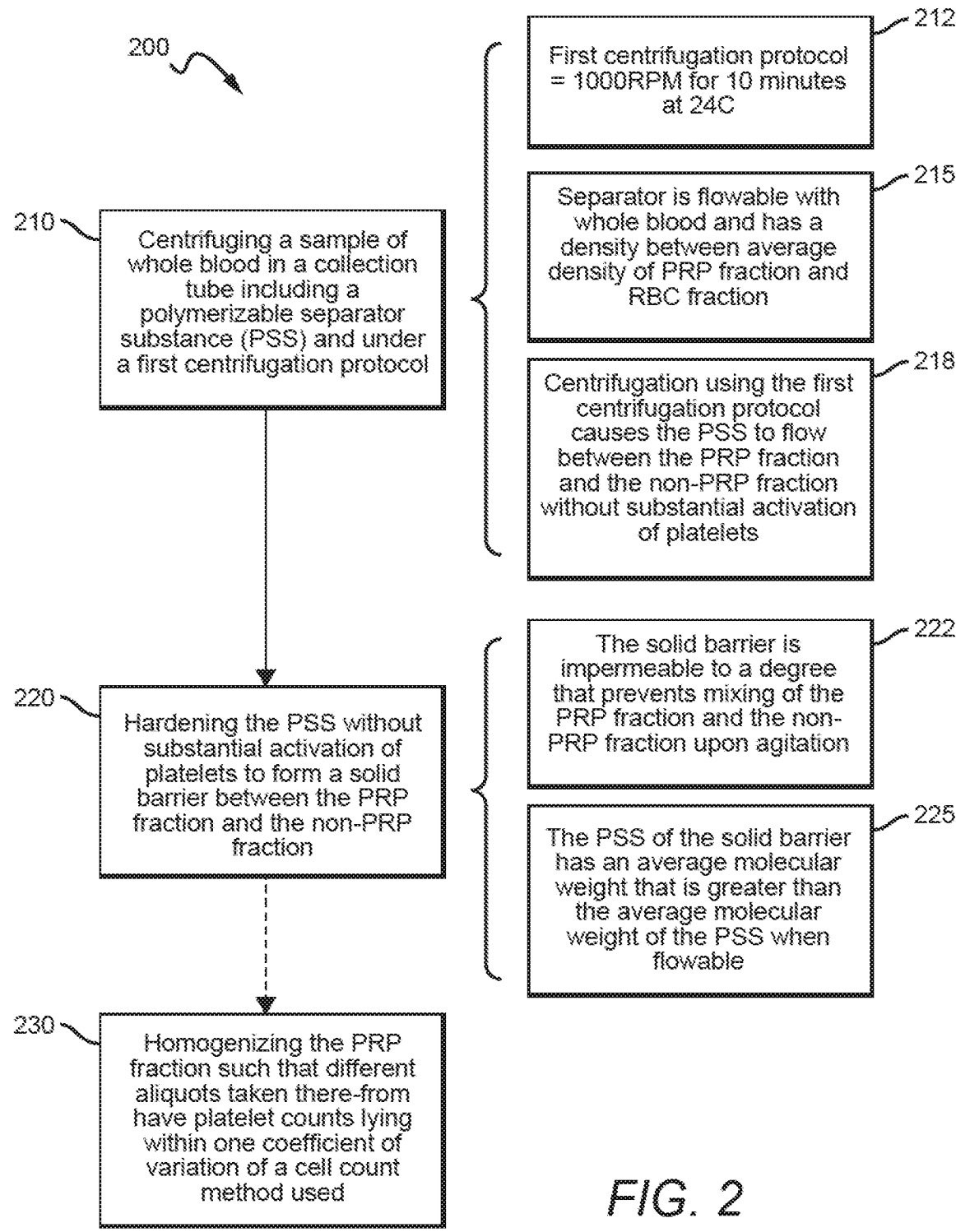
FIG. 2 is a schematic illustration of a method of separating a platelet rich plasma fraction from a sample of whole blood.

FIG. 2 illustrates a method 200 of separating a PRP fraction from a sample of whole blood in a collection tube including a polymerizable separator substance (PSS). While any suitable amount of the separator substance can be included in the tube's lumen, it is preferred that no more than about 1 ml or 2 grams of the separator substance be included per 10 ml volume of the tube.

Method 200 includes the step of centrifuging the sample of whole blood in the collection tube including the PSS using a centrifugation protocol as shown in step 210. Any suitable centrifugation protocol that is sufficient to cause the PSS to flow between two fractions of a sample is contemplated, including for example, centrifugation for ten minutes at 24° C. and 1000 RPM as shown in step 212. Other examples of suitable centrifugation protocols could include: a centrifugation time of between one minute and thirty minutes, inclusive, at between 500 RPM and 5000 RPM, inclusive; or a centrifugation time of between five minutes and twenty minutes, inclusive, at between 700 RPM and 3600 RPM, inclusive. As is well known in the art, centrifugation conditions determine the sedimentation and sedimentation rate of the platelets. The PHOSITA will be able, without undue experimentation, to determine the appropriate applied G forces and time to achieve a desired yield of platelets above the PSS. Therefore, an increase or decrease in desired yields can be readily achieved using the above considerations.

The below Table 2A illustrates some of the centrifugation protocols used in separating PRP from a sample of whole blood using a PSS of the inventive subject matter. The LAI composition included 100% L, 1% A, and 0.10% I.

TABLE 2A

Centrifugation Protocols

|  | Time (minutes) | RCF (g) | Platelet increase | RBC depletion |
|---|---|---|---|---|
| LAI | 5 | 300 | 186 | 99 |
| LAI | 5 | 300 | 202 | 99 |
| LAIR (5% R) | 5 | 300 | 250 | 99 |
| LAIR (5% R) | 5 | 300 | 233 | 99 |
| LAI | 12 | 200 | 122 | 99 |
| LAI | 12 | 200 | 119 | 99 |
| LAIR (5% R) | 12 | 200 | 132 | 99 |
| LAIR (5% R) | 12 | 200 | 139 | 99 |
| LAI | 10 | 150 | 144 | 98 |
| LAI | 10 | 150 | 119 | 98 |
| LAIR (5% R) | 10 | 150 | 122 | 99 |
| LAIR (5% R) | 10 | 150 | 125 | 99 |
| LAI | 20 | 150 | 133 | 99 |
| LAI | 20 | 150 | 98 | 99 |
| LAIR (5% R) | 20 | 150 | 122 | 99 |
| LAIR (5% R) | 20 | 150 | 114 | 99 |
| LAI | 10 | 300 | 180 | 99 |
| LAI | 10 | 300 | 190 | 99 |
| LAIE | 10 | 300 | 200 | 97 |
| LAIE (E 200 mM) | 10 | 300 | 210 | 99 |

The below Table 2B illustrates some of the centrifugation protocols used in separating BMAF from a bone marrow aspirate using a PSS of the inventive subject matter.

TABLE 2B

| Sample 1 (700 RPM, 15 mm): |
|---|
| Pre-spin platelet count: 166 × 10^3/uL |
| Post spin platelet count: 219 × 10^3/uL |
| Factor of increase: 1.32 |
| Sample 2 (600 RPM, 20 min): |
| Pre-spin platelet count: 41 × 10^3/uL |
| Post spin platelet count: 51 × 10^3/uL |
| Factor of increase: 1.24 |
| Sample 3 (1500 RPM, 5 min) |
| Pre-spin platelet count: 236 × 10^3/uL |
| Post spin platelet count: 260 × 10^3/uL |
| Factor of increase: 1.1 |
| Sample 4 (700 RPM, 10 min) |
| Pre-spin platelet count: 61 × 10^3/uL |
| Post spin platelet count: 67 × 10^3/uL |
| Factor of increase: 1.09 |

In most preferred embodiments, the PSS will be flowable with at least one of the whole blood and the bone marrow aspirate, and have a density that is at least one of (a) between an average density of a PRP fraction and an average density of a non-PRP fraction in accordance with step 215, and (b) between an average density of a BMAF and an average density of a non-BMAF fraction.

To achieve a desired initial density, it is contemplated that the density of the separator substance may be adjusted by virtue of molecular composition, or by inclusion of appropriate filler materials (e.g., silica, latex, or other inert material). Adjusting the density of a PSS may be desirable to separate different types of cells (e.g., platelets, stem cells, RBCs, WBCs) via centrifugation. All commercially suitable density adjusters are contemplated, including for example, Ebecryl 113.

Additionally or alternatively, centrifugation under a suitable protocol can cause the PSS to flow between the two fractions, for example, the PRP fraction and the non-PRP fraction, without substantial activation of platelets in accordance with step 218. It is contemplated that where the PSS is used for separation of a sample of a different fluid, or for separation of a sample of whole blood into fractions other than a PRP and non-PRP fraction, it is contemplated that the PSS could have a density between an average density of a first fraction to be separated and an average density of a second fraction to be separated.

As used herein, centrifugation using a first centrifugation protocol to cause the PSS to flow between two fractions of a sample without substantial activation of platelets means that the platelets retain function to within 15%, more preferably within 10%, of what would be retained by platelets during an otherwise identical centrifugation protocol as the first centrifugation protocol where a PSS is not used (e.g., without any separator substance). Substantial activation of platelets is measurable, among other things, based on the ability of platelets in the PRP fraction, non-PRP fraction, or both, to aggregate to at least one of Ristocetin and Collagen.

Method 200 also includes step 220 of hardening the PSS without substantial activation of platelets to form a solid barrier between the fractions, for example, the PRP fraction and the non-PRP fraction. Depending on the formulation of the separator substance, it is contemplated that the mode or mechanism of polymerization can vary considerably. While the discussion herein is directed primarily towards UV energy polymerization, all known methods of polymerization are deemed suitable for use herein. For example, contemplated polymerizations include various radical or cationic polymerizations (e.g., using photolabile compounds, radical starters, etc.), condensation polymerization, esterification, amide formation and so forth. Reactive groups can include acid groups, most preferably mono- and dicarboxylic groups), conjugated diene groups, aromatic vinyl groups, and alkyl(meth)acrylate. The polymerization can advantageously be fully supported by reactive groups of the monomers or oligomers of the separator substance, but additional reagents may also be suitable, including radical starters.

The step of hardening can advantageously form a solid barrier between the PRP fraction and the non-PRP fraction (or other separated fractions) that is stationary with respect to the collection tube. Viewed from another perspective, a solid barrier can be formed that is not dislodged from its position within the tube when the tube is manually shaken, when the tube is centrifuged to re-homogenize a separated fraction, or when the separated fraction is removed via pipette, transfer device or decanting. Additionally, the solid barrier can be impermeable to a degree that prevents mixing of the separated fractions upon agitation as shown in step 222. The PSS of the solid barrier will have an average molecular weight that is greater than the average molecular weight of the PSS when flowable with the whole blood in accordance with step 225.

As used herein, hardening the polymerizable separator substance without substantial activation of platelets means that the platelets retain function to within 15%, more preferably within 10%, of what would be retained by platelets where PSS is not used and where there is no step of hardening.

The solid barrier advantageously enables a step of removing at least 90%, more preferably at least 95% and most preferably 100% of the PRP or other separated fraction from the collection tube without remixing the fractions (e.g., without remixing the PRP fraction with the non-PRP fraction). This could be achieved by removing the PRP fraction as is from the collection tube (e.g., by pouring out, pipetting, etc.), or by including a saline or other fluid to the tube to assist in removing the entire PRP fraction. Additionally or alternatively, this could be achieved using a transfer device of the inventive subject matter as described below.

Method 200 could optionally include a step of homogenizing the PRP or other desired and separated fraction, after the step of hardening, such that different aliquots taken there-from have platelet counts lying within one coefficient of variation of a cell count method used. This can be highly beneficial in providing reproducibility and uniformity. Homogenizing the PRP fraction can be accomplished using any suitable methods, including for example, mechanical stirring, bubble stirring, turning the tube upside down or otherwise agitating, or triturating through wide mouth pipette.

Platelet Recovery

Many in the cosmetic and health industries have found that PRP having 200-250% of a platelet concentration of a sample of blood is optimal. It is also desirable to obtain purified or concentrated platelets or other desirable components while maintaining cell integrity during centrifugation. Increasing the viable platelet count would be desirable for therapeutic uses, and would presumably correlate to increased counts for other desirable cells.

Collection tubes previously used (e.g., purple top BD Vacutainers with no separator substance) to recover fractions of whole blood involve centrifuging blood to result in a serum fraction supernatant, an intermediate buffy layer, and a red blood cell fraction beneath the buffy layer. Such tubes and methods make it very difficult or even impossible to remove the supernatant without removing white cells from the buffy coat. On the other hand, where a gel is used, the result is a PRP or serum fraction depending on centrifugation protocol, then an intermediate gel layer, then a buffy coat, and a bottommost RBC fraction. Again, it is very difficult if not impossible to remove the entirety of the PRP or serum fraction without aspirating the gel with the PRP or serum. And in either event, there is a significant maldistribution of platelets in the PRP fraction.

The PSS and methods of the inventive subject matter advantageously allow for platelet recovery at various concentrations (including the 200-250% range), and also allow for use of the entirety of the PRP supernatant. Table 3 below illustrates that platelet yield using LAI or LAIR was at least as good as when using a control. Table 3 also illustrates that the same red blood cell depletion could be achieved using LAI or LAIR as when using the control.

TABLE 3

Blue Top (sodium citrate), Glass Tube, Fresh Blood, 30 second UV Exposure
Gel Composition = L (100%); A (1.00%); I (0.10%); R (5%)

|           | RCF (g) | Time (min) | Platelet (pre) | Platelet (post) | % Platelet Increase | RBC (Pre) | RBC (Post) | % RBC Depletion |
|-----------|---------|------------|----------------|-----------------|---------------------|-----------|------------|-----------------|
| Control 1 | 300     | 5          | 198            | 435             | 220                 | 4.19      | 0.03       | 99              |
| Control 2 | 300     | 5          | 216            | 462             | 214                 | 4.71      | 0.04       | 99              |
| LAI 1     | 300     | 5          | 205            | 381             | 186                 | 4.22      | 0.03       | 99              |
| LAI 2     | 300     | 5          | 194            | 392             | 202                 | 4.16      | 0.03       | 99              |
| LAIR 1    | 300     | 5          | 192            | 480             | 250                 | 4.18      | 0.03       | 99              |
| LAIR 2    | 300     | 5          | 201            | 469             | 233                 | 4.17      | 0.06       | 99              |

Red Top, Glass Tube, Pooled Blood, 30 second UV Exposure
Gel Composition = L (100%); A (1.00%); I (0.10%); R (5%)

|           | RCF (g) | Time (min) | Platelet (pre) | Platelet (post) | % Platelet Increase | RBC (Pre) | RBC (Post) | % RBC Depletion |
|-----------|---------|------------|----------------|-----------------|---------------------|-----------|------------|-----------------|
| Control 1 | 300     | 5          | 193            | 333             | 173                 | 1.96      | 0.03       | 98              |
| Control 2 | 300     | 5          | 122            | 186             | 152                 | 2.05      | 0.04       | 98              |
| LAI 1     | 300     | 5          | 117            | 175             | 150                 | 2.02      | 0.03       | 99              |
| LAI 2     | 300     | 5          | 141            | 267             | 189                 | 2.73      | 0.03       | 99              |
| LAIR 1    | 300     | 5          | 114            | 197             | 173                 | 2.11      | 0.03       | 99              |
| LAIR 2    | 300     | 5          | 121            | 195             | 161                 | 2.13      | 0.06       | 97              |

Blue Top (sodium citrate), Glass Tube, Pooled Blood, 30 second UV Exposure
Gel Composition = L (100%); A (1.00%); I (0.10%); R (5%)

|           | RCF (g) | Time (min) | Platelet (pre) | Platelet (post) | % Platelet Increase | RBC (Pre) | RBC (Post) | % RBC Depletion |
|-----------|---------|------------|----------------|-----------------|---------------------|-----------|------------|-----------------|
| Control 1 | 200     | 12         | 121            | 155             | 128                 | 2.20      | 0.03       | 99              |
| Control 2 | 200     | 12         | 143            | 165             | 115                 | 2.08      | 0.03       | 99              |
| LAI 1     | 200     | 12         | 134            | 164             | 122                 | 2.19      | 0.03       | 99              |
| LAI 2     | 200     | 12         | 138            | 164             | 119                 | 2.14      | 0.03       | 99              |
| LAIR 1    | 200     | 12         | 122            | 161             | 132                 | 2.18      | 0.03       | 99              |
| LAIR 2    | 200     | 12         | 122            | 169             | 139                 | 2.07      | 0.03       | 99              |
| LAI 1     | 150     | 10         | 171            | 247             | 144                 | 2.58      | 0.04       | 98              |
| LAI 2     | 150     | 10         | 177            | 211             | 119                 | 2.04      | 0.05       | 98              |
| LAIR 1    | 150     | 10         | 187            | 228             | 122                 | 1.8       | 0.05       | 97              |
| LAIR 2    | 150     | 10         | 198            | 248             | 125                 | 1.54      | 0.05       | 97              |
| LAI 1     | 150     | 20         | 183            | 243             | 133                 | 2.39      | 0.03       | 99              |

TABLE 3-continued

| | | | | | | | | |
|---|---|---|---|---|---|---|---|---|
| LAI 2 | 150 | 20 | 142 | 139 | 98 | 1.69 | 0.02 | 99 |
| LAIR 1 | 150 | 20 | 123 | 150 | 122 | 1.62 | 0.02 | 99 |
| LAIR 2 | 150 | 20 | 128 | 146 | 114 | 1.6 | 0.02 | 99 |

Table 4 below illustrates that platelet yield using LAI or LAIE was at least as good as when using a control. Table 4 also illustrates that the same or similar white blood cell depletion could be achieved using LAI or LAIE as when using the control.

The compositions (LAI and LAIE) tested are composed of the following:

| | LAI | LAIE |
|---|---|---|
| L | 100% | 100% |
| A | 1% | 1% |
| I | 0.10% | 0.10% |
| E | — | 200 mM |

The manual differential of LAI was as follows: 8% neutrophils, 80% lymphocytes, 10% monocytes, 2% eosinophils; The manual differential of LAIE was as follows: 5% neutrophils, 89% lymphocytes, 5% monocytes, 1% eosinophils.

TABLE 4

| Sample ID | Control 1 WB | Control 2 WB | Avg Control WB | Control 1 Plasma | Control 2 Plasma | Avg Control Plasma | Control 1 Exp UV | Control 2 Exp UV | Avg Control Exp UV | LAI Plasma | % Depletion | LAIE Plasma |
|---|---|---|---|---|---|---|---|---|---|---|---|---|
| Centrifuge | No | No | | Yes | Yes | | Yes | Yes | | Yes | | Yes |
| UV-exposure | No | No | | No | No | | 1:45 min at 1", | 1:45 min at 1", 25% | 1:45 min at 1", 25% | 1:00 min at 1", 25% | | 1:45 min at 1", 25% |
| WBC [10^3/uL] | 3.6 | 3.66 | 3.63 | 0 | 0.01 | 0.005 | 0.10 | 0.16 | 0.13 | 0.06 | 98.3 | 0.06 |
| RBC [10^6/uL] | 3.97 | 3.93 | 3.95 | 0.02 | 0.02 | 0.02 | 0.01 | 0.01 | 0.01 | 0.03 | 99.2 | 0.02 |
| HGB [g/dL] | 12.8 | 12.6 | | 0 | 0 | | 0.00 | 0 | 0 | 0 | | 0 |
| H CT [%] | 38.1 | 37.6 | | 0.1 | 0.1 | | 0.10 | 0.1 | 0.1 | 0.1 | | 0.1 |
| MCV [fL] | 96 | 95.7 | | 50 | 50 | | 100.00 | 100 | | 33.3 | | 50 |
| MCH [pg] | 32.2 | 32.1 | | 0.0 | 0.0 | | 0.0 | 0.0 | | 0.0 | | 0.0 |
| MCHC [g/dL] | 33.6 | 33.5 | | 0.0 | 0.0 | | 0.0 | 0.0 | | 0.0 | | 0.0 |
| RDW-SD [fL] | 45.7 | 45.8 | | — | — | | — | — | | — | | — |
| RDW-CV [%] | 12.8 | 13 | | — | — | | — | — | | — | Platelet Factor Increase | — |
| PLT [10^3/uL] | 130 | 139 | 134.5 | 182 | 156 | | 186.00 | 177 | | 301 | 2.2 | 275 |
| MPV [fL] | 11.3 | 11 | | 11 | 10.8 | | 10.50 | 10.5 | | 11.2 | | 11 |

(also: Control 1 Exp UV PLT = 186.00, LAIE column final two values 275 and 2.0 for Platelet Factor Increase)

Table 5 shows platelet yield and white blood cell depletion under a centrifugation protocol as follows: 1000 RPM for ten minutes at 24 C. There was a slight increase in platelet yield and similar white blood cell/red blood cell depletion.

The compositions (LAI and LAIE) tested are composed of the following:

|   | LAI   | LAIE   |
|---|-------|--------|
| L | 100%  | 100%   |
| A | 1%    | 1%     |
| I | 0.10% | 0.10%  |
| E | —     | 200 mM |

The experiments were conducted in Sodium Citrate Tubes.

TABLE 5

| Sample ID | Control1 | Control2 | Avg Controls | LAI 1 | Cntrl 1 plasma | Ctrl 2 plasmaa |
|---|---|---|---|---|---|---|
| Centrifuge | No | No |  | No | Yes | Yes |
| UV-exposure | No | No |  | No | No | No |
| WBC [10^3/uL] | 6.86 | 6.46 | 6.66 | 6.45 | 0.09 | 0.03 |
| RBC [10^6/uL] | 4.17 | 4.22 | 4.20 | 4.35 | 0.01 | 0.01 |
| HGB [g/dL] | 12.9 | 13 | 13.0 | 13.2 | 0 | 0 |
| HCT [%] | 38.3 | 38.9 | 38.6 | 40.3 | 0.1 | 0.1 |
| MCV [fL] | 91.8 | 92.2 | 92.0 | 92.6 | 100 | 100 |
| MCH [pg] | 30.9 | 30.8 | 30.9 | 30.3 | 0.0 | 0.0 |
| MCHC [g/dL] | 33.7 | 33.4 | 33.6 | 32.8 | 0.0 | 0.0 |
| RDW-SD [fL] | 44.2 | 44 | 44.1 | 44.9 | — | — |
| RDW-CV [%] | 13.2 | 13.2 | 13.2 | 13.2 | — | — |
| PLT [10^3/uL] | 226 | 215 | 220.5 | 226 | 385 | 400 |
| MPV [fL] | 8.9 | 8.8 | 8.9 | 8.4 | 9.4 | 9.3 |

| Avg Ctrl plasma | Post UV ctrl 1 | Post UV ctrl 2 | Avg Post UV Ctrl | LAI 1 plasma |
|---|---|---|---|---|
|  | Yes 1:45 min at 1", 25% | Yes 1:45 min at 1", 25% |  | Yes 1:00 min at 1", 25% |
| 0.06 | 0.10 | 0.07 | 0.09 | 0.21 |
| 0.01 | 0.02 | 0.02 | 0.02 | 0.02 |
| 0 | 0.00 | 0 | 0 | 0 |
| 0.1 | 0.10 | 0.1 | 0.1 | 0.1 |
| 100 | 50.00 | 50 | 50 | 50 |
| 0 | 0.0 | 0.0 | 0 | 0.0 |
| 0 | 0.0 | 0.0 | 0 | 0.0 |
| — | — | — |  | — |
| — | — | — |  | — |
| 392.5 | 336.00 | 393 | 364.5 | 449 |
| 9.35 | 9.90 | 9.5 | 9.7 | 8.9 |

| Sample ID | LAI 2 plasma | Avg LAI | LAIE 1 plasma | LAIE 2 plasma | Avg LAIE | Ctrl depletion RBC, WBC | % Depletion LAI | % Depletion LAIE |
|---|---|---|---|---|---|---|---|---|
| Centrifuge | Yes |  | Yes | Yes |  |  |  |  |
| UV-exposure | 1:00 min at 1", 25% |  | 1:00 min at 1", 25% | 1:45 min at 1", 25% |  |  |  |  |
| WBC | 0.15 | 0.18 | 0.23 | 0.02 | 0.125 | 99.10 | 97.30 | 98.12 |
| RBC | 0.01 | 0.015 | 0.02 | 0.01 | 0.015 | 99.76 | 99.64 | 99.64 |
| HGB [g/dL] | 0 | 0 | 0 | 0 | 0 |  |  |  |
| HCT [%] | 0 | 0.05 | 0.1 | 0 | 0.05 |  |  |  |
| MCV [fL] | 0 | 25 | 50 | 100 | 75 |  |  |  |
| MCH [pg] | 0.0 | 0 | 0.0 | 0.0 | 0.0 |  |  |  |
| MCHC [g/dL] | — | 0.0 | 0.0 | 0.0 | 0.0 |  |  |  |
| RDW-SD [fL] | — | — | — | — | — |  |  |  |
| RDW-CV [%] | — | — | — | — | — |  | Factor platelets increased |  |
| PLT | 394 | 421.5 | 456 | 439 | 447.5 | 1.8 | 1.9 | 2.0 |
| MPV [fL] | 8.8 | 8.85 | 9 | 9 | 9 |  |  |  |

Recovery of a Homogenous PRP Fraction

The PSS of the inventive subject matter provides an additional advantage of enabling preparation of a substantially homogenous BMAF, PRP, or other fraction. Applicant compared the recovery of cell-free DNA in 3 tube types and determined that aliquots taken from an unmixed specimen would lead to variable results. Viewed from a different perspective, if a user aliquots plasma from a non-gel tube without mixing, the aliquots will be highly variable. If a user aliquots the plasma from the tube and mixes it outside of the tube, the results may be more reproducible but the recovery is worse.

Figure 3:
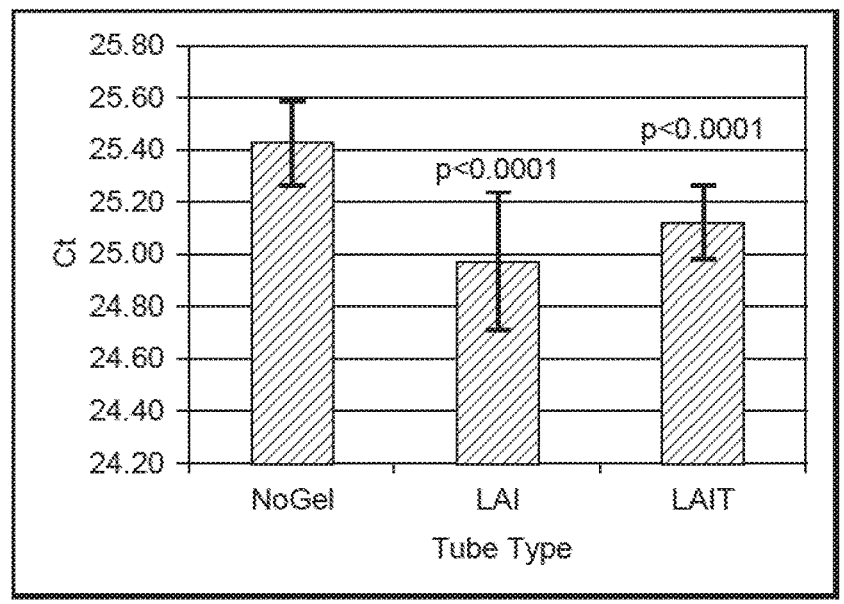
FIG. 3 shows the "Cts" (cycle threshold) of the control, the tube with LAI, and the tube with LAIT.
Figure 5:
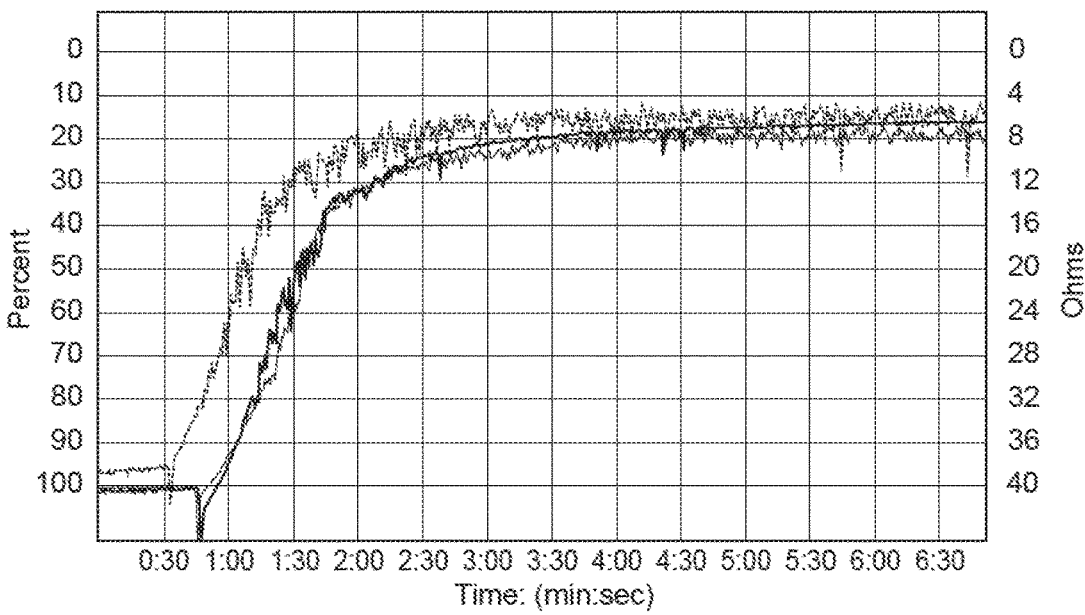
FIG. 5 shows aggregation of a control, LAI and LAIE to Ristocetin.

The 3 tube types tested are as follows: control ("No gel"), tube with LAI photogel and tube with LAIT photogel where L=oligomer, A=additol BDK photoinitiator, I=phenothiazine stabilizer, and T=tempo nitroxide. FIG. 3 shows the "Cts" (cycle threshold) of the control, the tube with LAI, and the tube with LAIT. The lower Ct of LAI and LAIT as compared to the control indicates better recovery as compared to the control. FIG. 5 also shows that the results using LAI and LAIT were similarly reproducible as the control. N=4 for each tube type.

The protocol used is as follows: pooled blood was mixed and loaded by pipette into each of the nine tubes. The photogel tubes were preloaded with either LAI or LAIT. All tubes were centrifuged at room temperature for 10 minutes at 3000 RPM. Following centrifugation, the photogel tubes were exposed to UV light in a light box for 1 minute. The plasma from each tube was withdrawn, and for tubes including the solidified barrier, all plasma was withdrawn. For the control tube with no gel, care was taken not to disrupt the cell layer which required leaving some plasma behind (approximately 100 uL). The plasma was sent to the molecular pathology lab for DNA-Braf analysis. There, the four tubes were further aliquotted into three samples each. Thus the variability shown is inclusive of the process of dividing the plasma from each tube three ways.

Plasma obtained from an EDTA tube with no gel was manually sampled at the top layer, bottom (near cells) layer, and middle portion. The plasma was mixed by vortex and sampled again ("mixed"). The melt curves shown below demonstrate that the cfDNA recovered varies with manual sampling. Cell free DNA was used as a proxy marker to platelet recovery.

Figure 4:
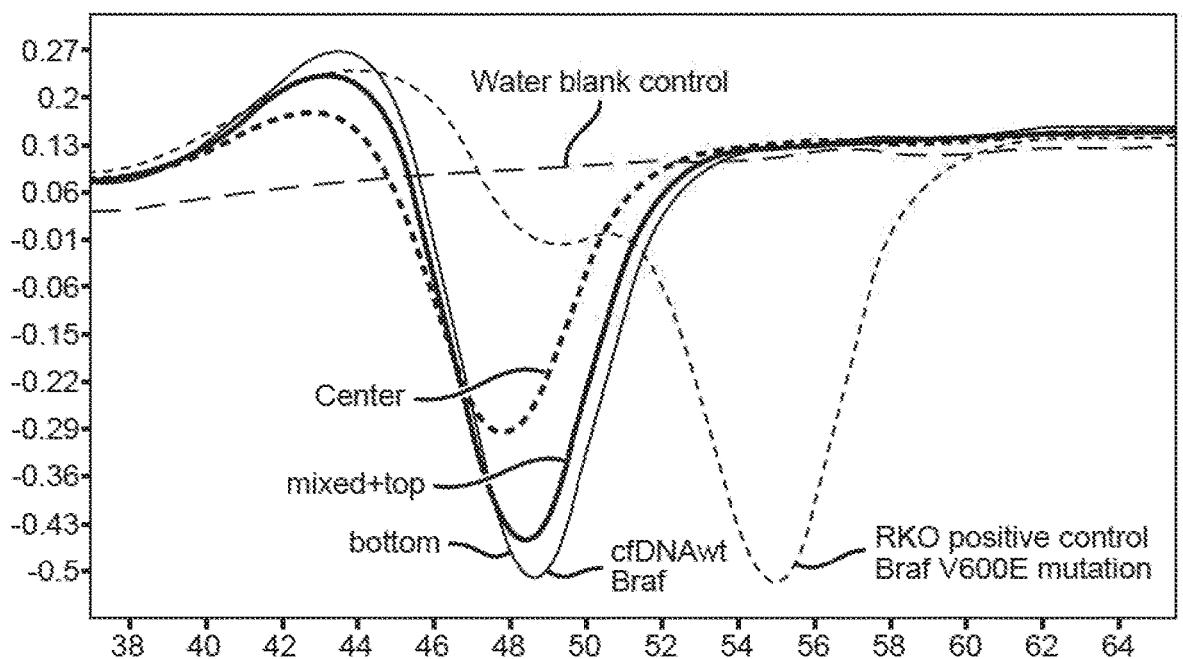
FIG. 4 shows the non-reproducability of cfDNA counts taken from unmixed plasma.

In the example shown in FIG. 4, the aliquot taken from the bottom layer of the unmixed plasma had more cfDNA than aliquot taken from a center portion or a mixed top portion (deeper trough indicates greater recovery).

Because the methods described herein include the use of a PSS that is hardened to form a solid barrier, the PRP fraction can be mixed inside the collection tube in which it is obtained or separated, which allows for homogenizing of the PRP fraction in the collection tube without exposure to an environment outside of the collection tube. It should be appreciated that the PSS allows a user to obtain a homogenous reliable count of platelets because amounts obtained from different portions of the tube can be within one coefficient of variation of a cell count method used.

Platelet Viability

As discussed above, Applicants were able to demonstrate that similar or even improved platelet recovery could be achieved using methods and PSSs of the inventive subject matter. It is known in the art that solid barriers with long polymers, while often improving platelet recovery, interfere with platelet function. The experiments and data provided below show that Applicant's methods and PSSs allow for optimal platelet recovery while maintaining viability of the platelets.

Platelet viability was tested by observing platelet aggregation to specific agonists on the Chrono-log aggregometer. The PRP was obtained by centrifuging whole blood loaded into a control tube (BD sodium citrate tube, no gel), LAI tube (BD sodium citrate to which LAI was added), and LAIE tube (BD sodium citrate tube with LAIE added). The photogel tubes were exposed to UV light after centrifugation to solidify the barrier. The PRP was aliquotted and diluted with platelet poor plasma to a platelet concentration required by the Chrono-log standard operating procedure. Below are example curves of platelet aggregation to Ristocetin and Collagen. Collagen is a strong agonist that induces aggregation, secretion of platelet granules and thromboxane synthesis, thus it is an inclusive test for platelet viability.

As illustrated in FIG. 5, no significant different in aggregation to Ristocetin was shown between the control, LAI and LAIE.

Figure 6:
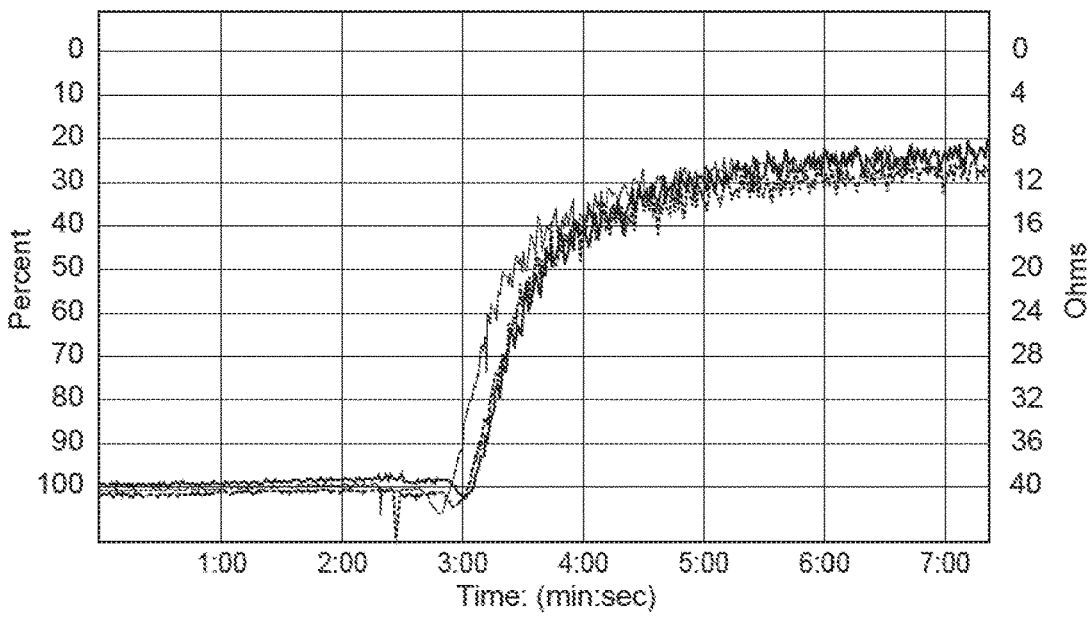
FIG. 6 shows aggregation of a control, LAI and LAIE to Collagen.

As illustrated in FIG. 6, no appreciable difference is seen in platelet aggregation curves for platelets to Collagen from control, LAI or LAIE curves, which indicates that the LAI and LAIE do not substantially affect platelet functionality.

Figure 7:
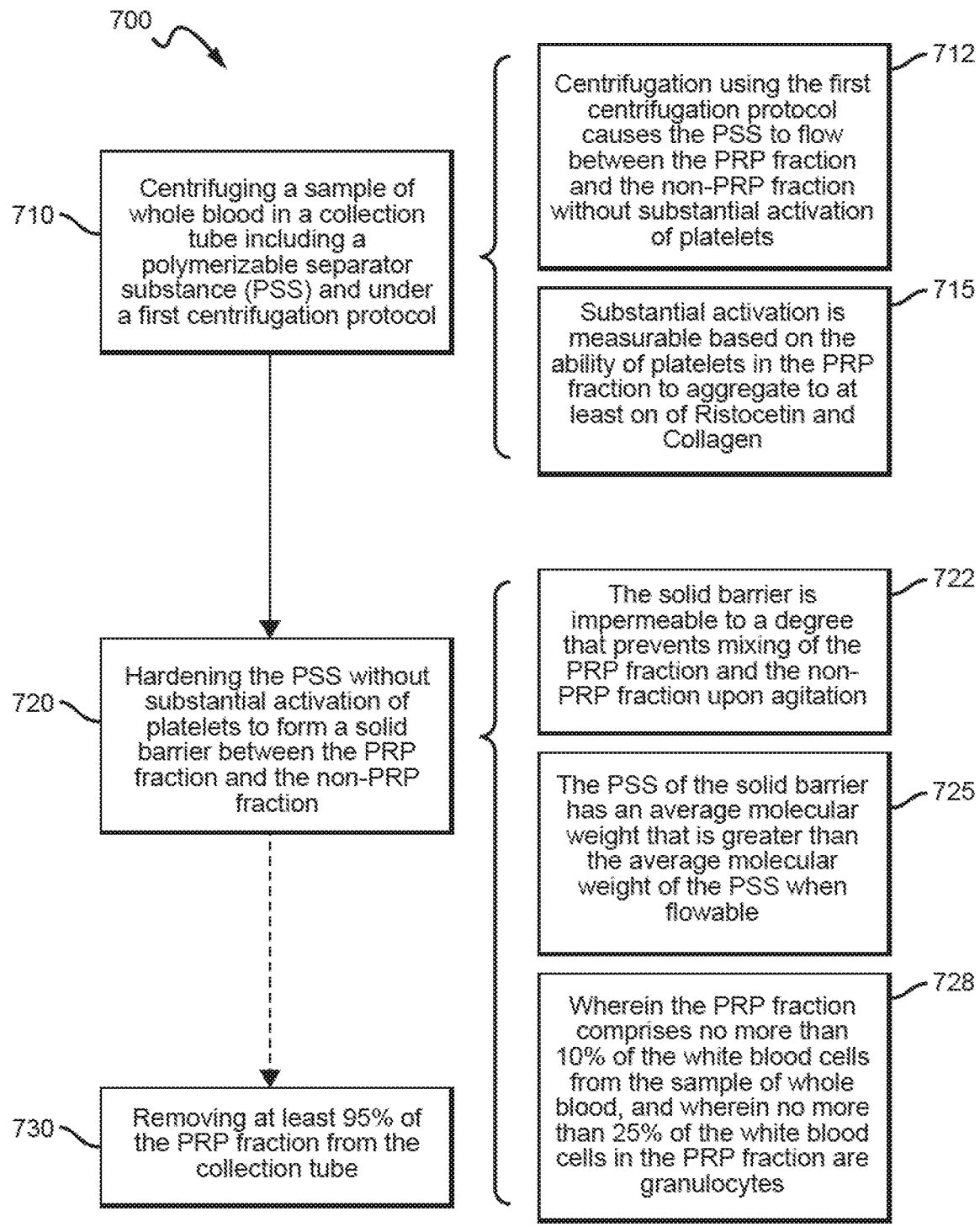
FIG. 7 is a schematic illustration of another method of separating a platelet rich plasma fraction from a sample of whole blood.

FIG. 7 illustrates another method 700 of separating a PRP fraction from a sample of whole blood in a collection tube including a PSS that is flowable with whole blood and has a density between an average density of a PRP fraction and an average density of a non-PRP fraction of whole blood.

Method 700 includes the step of centrifuging the sample of whole blood in the collection tube including the PSS using a centrifugation protocol as shown in step 710. Similarly to the centrifugation step of method 200, centrifugation using a suitable centrifugation protocol will cause the PSS to flow between the PRP fraction and the non-PRP fraction without substantial activation of platelets as shown in step 712. Substantial activation is measurable based on the ability of platelets in the PRP fraction to aggregate to at least one of Ristocetin and Collagen as shown in step 715.

Method 700 further includes the step of hardening the PSS without substantial activation of platelets to form a solid barrier between the PRP fraction and the non-PRP fraction as shown in step 720. The PSS of the solid barrier will have an average molecular weight that is greater than the average molecular weight of the PSS when flowable with the whole blood (e.g., prior to the step of hardening) in accordance with step 725.

In some preferred methods, the solid barrier, after exposure to the UV energy, will be stationary with respect to the collection tube at an intermediate position below the PRP fraction and above the non-PRP fraction and be impermeable to a degree that prevents mixing of the PRP fraction and the non-PRP fraction upon agitation as shown in step 722. The solid barrier allows for removal of at least 90%, more preferably at least 95% and most preferably 100% of the PRP fraction from the collection tube. Viewed from a different perspective, method 700 includes an optional step of removing at least 95% of the PRP fraction from the collection tube in accordance with step 730.

The PRP fraction can advantageously comprise no more than 10% of white blood cells from the sample of whole blood. Additionally or alternatively, it is contemplated that no more than 25% of the white blood cells in the PRP fraction will be granulocytes. Viewed from another perspective, a significant reduction of WBCs (e.g., less than 60%, less than 70%, less than 80% or even less than 90%), and a significant reduction of granulocytes (e.g., less than 50%, less than 70%, less than 80% or even less than 90%) can be found in a PRP fraction as compared to the same sample volume in whole blood.

Method 700 could also comprise homogenizing the PRP fraction in the collection tube after the step of hardening. The homogenizing step could be performed immediately after hardening, within one hour of hardening, within one day of hardening, at least two days after hardening, at least five days after hardening, or even at least one month after hardening. Homogenizing the PRP fraction results in a substantially homogenous PRP fraction such that different aliquots taken there-from have platelet counts lying within one coefficient of variation of a cell count method used.

Figure 8:
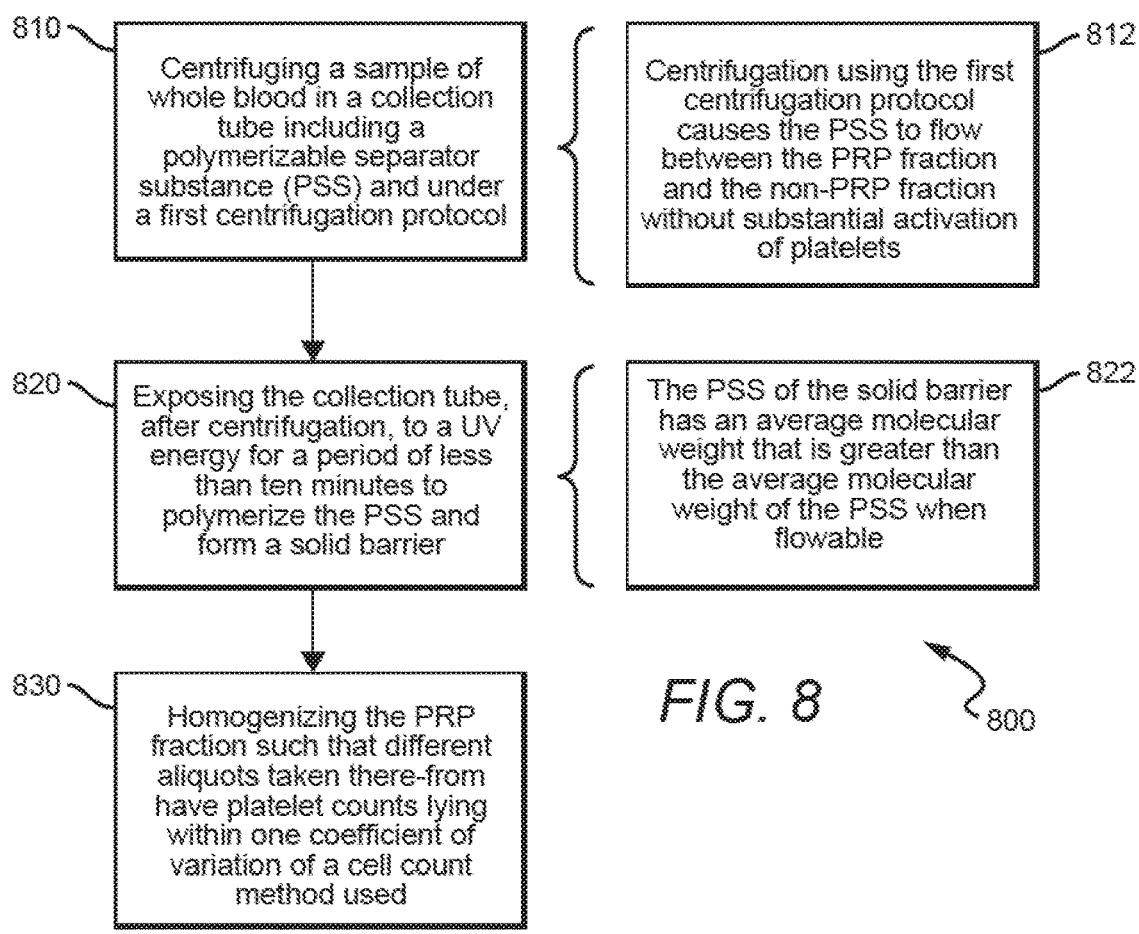
FIG. 8 is a schematic illustration of yet another method of separating a platelet rich plasma fraction from a sample of whole blood.

FIG. 8 illustrates yet another method 800 of separating a PRP fraction from a sample of whole blood in a collection tube including a PSS that is flowable with whole blood and has a density between an average density of a PRP fraction and an average density of a non-PRP fraction of whole blood.

It should be appreciated that a PRP fraction could have any suitable platelet concentration that is greater than a platelet concentration of a sample of whole blood from which it is obtained or separated. For example, a PRP fraction could comprise at least 150%, at least 200%, at least 250% or even greater platelet concentration of a platelet concentration of the sample from which it is obtained. Viewed from a different perspective, a PRP fraction could comprise between a 180% and 260% platelet concentration or between a 200% and 250% platelet concentration of a platelet concentration of the sample from which it is obtained.

Method 800 includes a step of centrifuging a sample of whole blood in a collection tube including a PSS and under a first centrifugation protocol as shown in step 810. Centrifugation under the first protocol can cause the PSS to flow between the PRP fraction and the non-PRP fraction, preferably without substantial activation of platelets as shown in step 812.

Method 800 also includes a step of exposing the collection tube, after centrifugation, to a UV energy for a period of less than ten minutes to polymerize the PSS and form a solid barrier as shown in step 820. The PSS of the solid barrier will have an average molecular weight that is greater than the average molecular weight of the PSS when flowable with the sample of whole blood as shown in step 822.

Method 800 further includes a step of homogenizing the PRP fraction in the presence of the solid barrier to form a substantially homogenous PRP fraction such that different aliquots taken there-from have platelet counts lying within one coefficient of variation of a cell count method used.

The methods described herein advantageously allow a user to separate fractions of different densities of a sample (e.g., blood) included in a collection tube with a PSS. The solid barrier allows for both homogeneity and reproducibility, and applicant has discovered that further advantages could be achieved by providing an adapter such that the tubes in which the fractions are separated never need to be opened.

Once a BMAF or PRP fraction is separated in a collection tube, it would be advantageous to transfer the fraction from the separation/preparation tube to another container while maintaining sterility of the sample. This could allow for home uses of the separated fraction, for example, as a PRP eye drop solution for the treatment of wounds, sores or other conditions.

FIGS. 9A-9I illustrate an embodiment of a contemplated transfer device 900 being used to transfer a separated substance (e.g., PRP, BMAF) from a first vacutainer to a second vacutainer. It should be appreciated, however, that transfer device 900 could be used to transfer any substance from any commercially suitable preparation container to any commercially suitable user container. As one non-limiting example, transfer device 900 could be used to transfer a PRP fraction of whole blood from a vacutainer to a sterile eye dropper container having a self-sealing septum.

Transfer device 900 includes a housing that at least partially encloses a base structure, a transfer needle, and a vent needle (902 and 904, respectively). The housing and a first portion of the base structure can be fixedly coupled or attached to one another and at least partially define a first internal section 910 and a second internal section 920 on opposite sides of the first portion.

Additionally or alternatively, the housing and the first portion of the base structure could be movably or even removably coupled to one another. Additionally or alternatively, the housing and a second portion of the base structure can be fixedly coupled or attached to one another. Additionally or alternatively, the housing and the second portion of the base structure can be movably coupled to one another. For example, the second portion of the base structure can be movably coupled to the first portion of the base structure that is fixedly coupled to the housing. As another example, the second portion of the base structure can be movably coupled to an inner wall of the housing, and the first portion of the base structure can be fixedly attached to an inner wall of the housing.

Where a portion of the base structure is movable, it should be appreciated that the volumes of the first and second internal sections do not change. Instead, the first and second internal sections should be viewed as the sections separated by the base structure when the different base structure portions are aligned side-by-side to the extent possible.

As illustrated, first internal section 910 can include a portion of transfer needle 902, and a portion of vent needle 904. Second internal section 920 only includes a portion of the transfer needle 902. Vent needle 902 only extends above the base, and is configured to pierce only a tube disposed within the first internal section 910. More specifically, transfer needle 904 can extend through a first portion of the transfer device base, and vent needle 902 can be attached to (but not extend through) a second portion of the transfer device base.

The second portion of the base including the second vent needle can be movable relative to the housing. Additionally or alternatively, vent needle 902 can be coupled to a vent 930 that extends through an elongated slot 925 of the housing. When vent needle 902 punctures a rubber stopper of the preparation tube, air can flow through vent 930, through vent needle 902, and into the preparation tube. The amount of vent needle 902 that is positioned within the first internal section 910 and thus can puncture a preparation tube can vary depending on the positioning of vent 930 through elongated slot 925, and the positioning of the second portion of the base relative to the housing.

Where the second portion of the base structure is movably coupled to the housing, it is contemplated that the vent could be fixedly coupled to the second portion of the base. The coupling of the needles, vent, and a moving second portion of the base structure to the housing can ensure that the vent needle (and air via the vent) does not enter a preparation tube 935 until the transfer needle has entered the transfer tube 940.

When the second portion of the base structure is fixedly coupled to the housing, it is contemplated that the vent could be movably (e.g., slidably) coupled to the second portion of the base. The coupling of the needles, vent, and the fixed section portion of the base structure to the housing can ensure that the vent needle does not enter the preparation tube 935 until the transfer needle has entered the transfer tube 940. The user could pierce a preparation tube and a transfer tube with the transfer needle (within first and second internal sections of the housing), and then slide the vent towards the first internal section 910 of the housing to pierce the preparation tube with the vent needle.

Additionally or alternatively, it should be appreciated that both the second portion of the base structure and the vent could be movable relative to the housing.

Figure 9F:
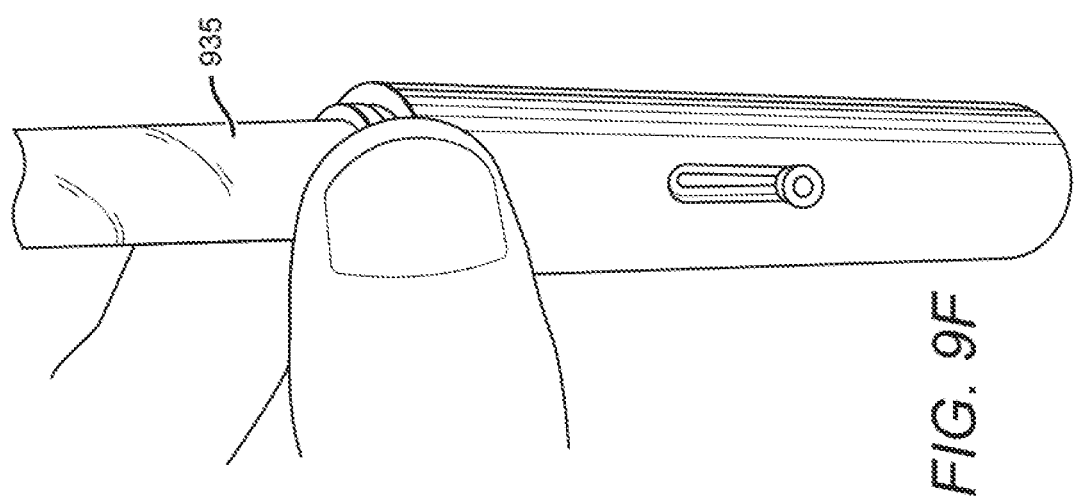
Figure 9E:
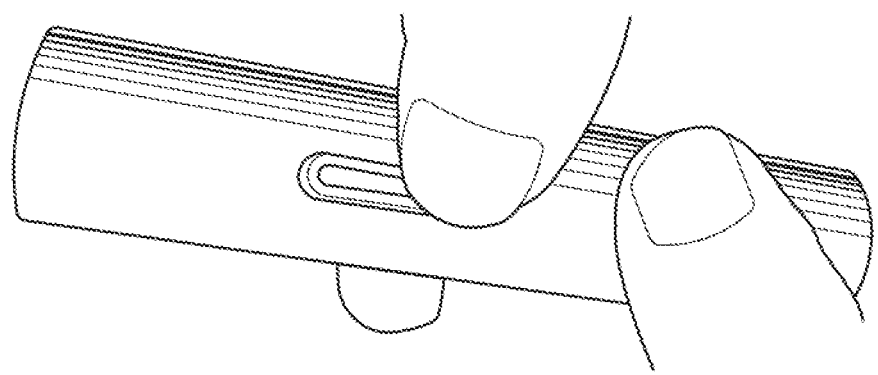

When transfer device 900 is used, vent 930 will preferably initially be in a configuration as shown in FIGS. 9E and 9F, at a lower edge of the slot towards the second internal section. In such a configuration, the vent 930 is placed within the slot at a position closest to the second internal portion of the housing. When preparation tube 935, which includes the sample to be transferred, is positioned at least partially within first internal section 910, the transfer needle could pierce its rubber septum, and the vent needle could remain outside of tube 935.

Figure 9D:
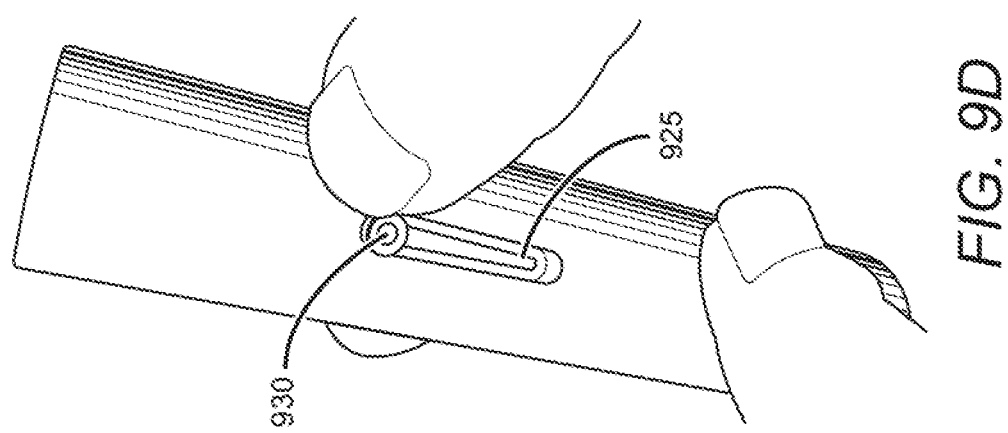

The sterile transfer tube 940 can then be partially inserted into second internal portion 920 such that the transfer needle pierces the self-sealing septum of tube 940 (or other container). As the transfer needle enters tube 940, it is contemplated that vent 930 and vent needle will be moved as shown in FIGS. 9D and 9G such that the second needle pierces a septum of tube 935.

As the vent needle pierces the septum of tube 935, air enters tube 935 via vent 930, and causes substantially all of the PRP from tube 935 to transfer to tube 940 via the transfer needle, as shown in FIGS. 9G, 9H and 9I.

FIGS. 10A-10E provide cross-sectional views of another transfer device of the inventive subject matter being used to transfer a separated substance from a first container to a second container.

In FIG. 10A, the preparation container (upper container) 1080 is being placed upside down into the first internal section 1050 of the transfer device. The preparation container 1080 includes a rubber stopper 1089, a serum fraction 1088, air 1086, a separator substance 1084, and a cell fraction 1082. Where the separator substance is a PSS of the inventive subject matter, it should be appreciated that the preparation container can advantageously be placed upside down into the first internal section without being dislodged or otherwise moved.

Similarly to device 900, device 1000 includes a housing (or safety shroud) 1010, a base structure, a transfer needle 1020 extending through first and second internal sections (1050 and 1060, respectively), and a movable vent needle 1030 coupled to a vent 1035 and extending from the base structure to the first internal section 1050.

Once the preparation container 1080 has been pierced by the transfer needle 1020, the evacuated tube (lower container) 1090 could be placed within the second internal section 1060 and pierced by the transfer needle 1020.

FIG. 10B illustrates the possible positioning of components within the transfer device after piercing of the preparation container with the transfer needle but prior to piercing of the preparation container with the vent needle. The transfer needle 1020 is held in place on a first part of the base structure with glue that is inserted through a hole 1045 in the housing.

The vent needle 1030 is coupled to a vent 1035 that preferably extends orthogonally to the vent needle. The vent 1035 could be coupled to a sliding or otherwise moving part of the base structure, and extend through a slot 1040 of the housing. Here, the vent 1035 is positioned through the slot 1040 at the end closest to the second internal portion 1060 of the housing.

In some preferred embodiments, the transfer needle will extend further into the second internal portion than the sliding part of the base structure even when the vent is positioned at the end of the slot closest to the second internal portion of the housing. This could help ensure that the transfer container (lower container) 1090 is pierced before the vent needle pierces the preparation container such that the PRP is not wasted. Rubber or other sleeves (e.g., 1022, 1032, and 1024) can be included to cover the exposed end portions of one or both needles to prevent contamination or to provide additional safety and sterility.

Figure 10C:
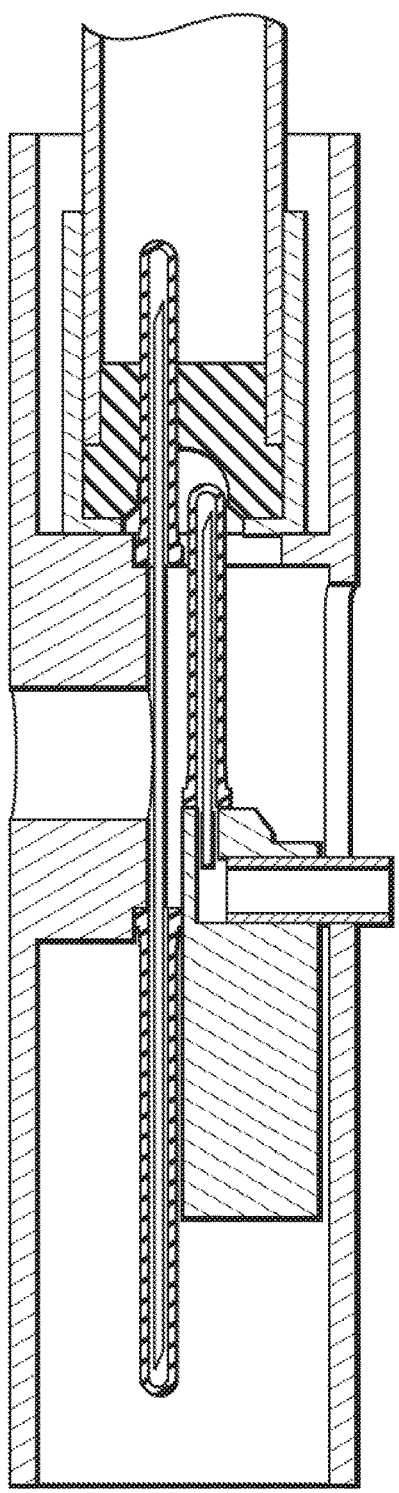
Figure 10D:
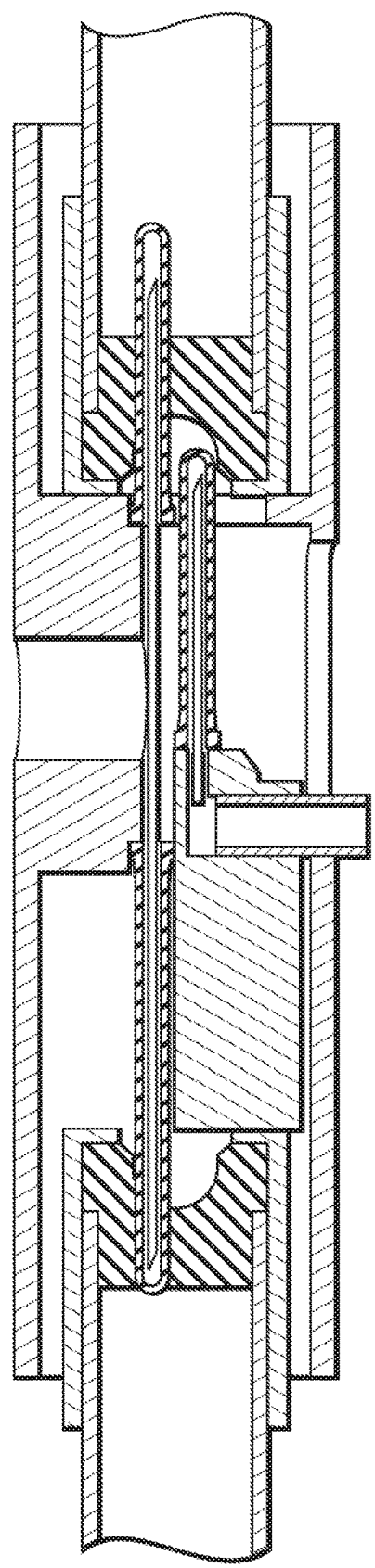
Figure 10E:
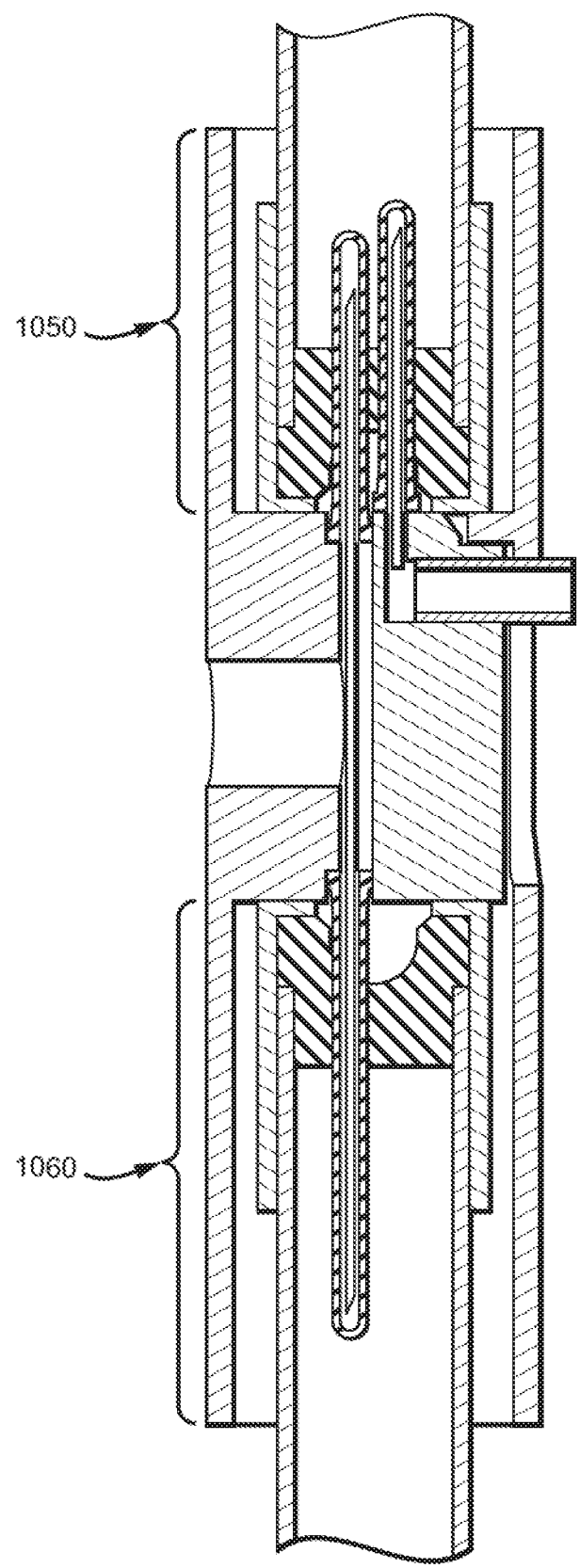

In FIG. 10C, the preparation container 1080 is pierced by the transfer needle 1020 in the first internal portion 1050 of the housing, and the vent needle 1030 remains positioned entirely outside of the preparation container 1080. In FIGS. 10D-10E, the transfer container 1090 is pierced by the transfer needle 1020 in the second internal portion 1060 of the housing, and moved towards the first internal portion 1050. While the transfer container 1090 is moved towards the first internal portion 1050, the moving part of the base, the vent 1035 and the vent needle 1030 are also moved towards the first internal portion 1050. The vent needle 1030 pierces the preparation container 1080, causing air to enter the preparation tube 1080 and force the serum 1088 into the transfer container 1090.

Figure 11A:
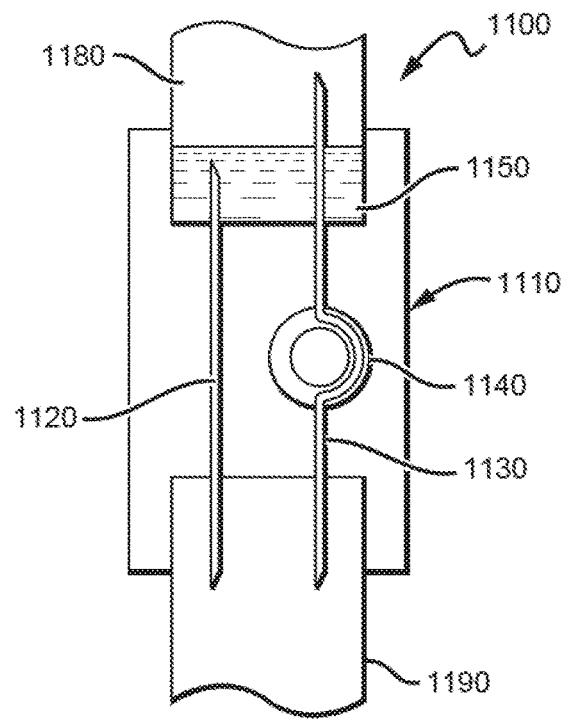
FIGS. 11A-11B illustrate an alternative transfer device of the inventive subject matter.
Figure 11B:
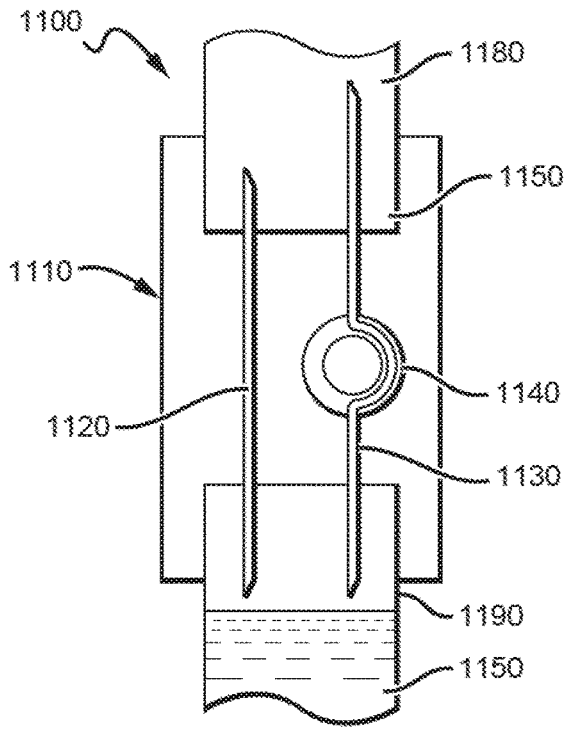

FIGS. 11A-11B provide an alternative transfer device 1100 that could be used to transfer fluid from a preparation container to another container.

In FIG. 11A, the transfer device 1100 comprises a serum transfer needle 1120 and an air transfer needle 1130 that each extend into first and second internal sections of a housing 1110. The preparation tube 1180 is at least partially placed in one end of the transfer device 1120, and an evacuated tube 1190 or eyedropper is at least partially placed in another end of the transfer device 1120 such that both a serum transfer needle 1120 and an air transfer needle 1130 ends are in both tubes. The end of the air transfer needle that is disposed positioned within the first internal section will preferably be inserted to a level above the serum 1150 in the preparation tube 1180. A peristaltic or other pump 1140 could operate to move air from the evacuated tube 1090 into the preparation tube 1080 via the air transfer needle 1130. This volume X of air removed from the evacuated tube creates a vacuum in the evacuated tube 1190 and the same volume X of serum 1150 can be pulled from the preparation tube 1180 into the evacuated tube 1190 via the serum transfer needle 1120. FIG. 11B shows how the volume X of the serum moves into the evacuated tube.

Figure 12A:
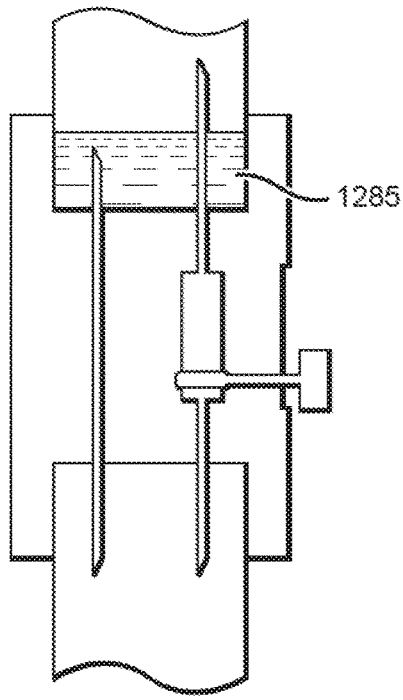
FIGS. 12A-12B illustrate another alternative transfer device.
Figure 12B:
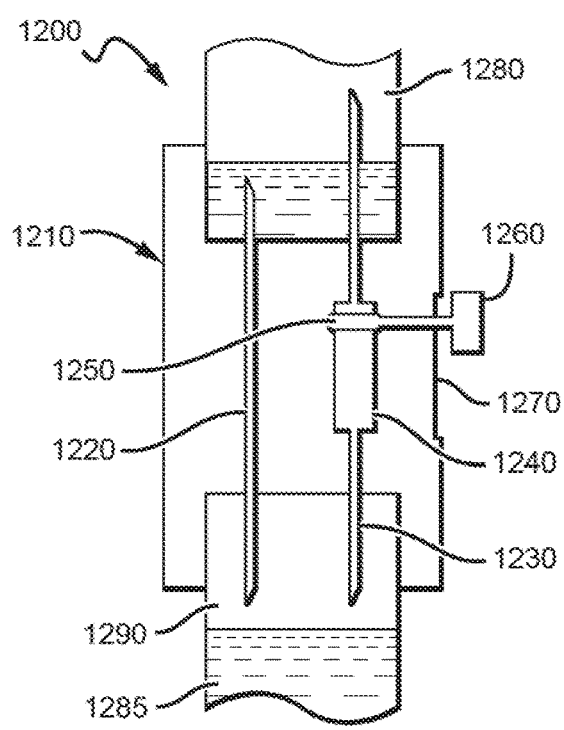

FIGS. 12A-12B provide yet another transfer device 1200 of the inventive subject matter including housing 1210. The transfer device is similar to the device of FIGS. 11A-11B. However, a pinching device 1250 in combination with a flexible tube 1240 is used in place of a pump. The pinching device can cause a volume Y of air to move into the preparation tube 1280 and, at the same time, cause the same volume Y of air to be pulled up from the evacuated tube 1290. This extra air in the preparation tube and the lower amount of air in the evacuated tube can cause the same volume Y of the serum 1285 to move from the preparation tube to the evacuated tube via the serum transfer needle 1220.

The mechanism illustrated in FIGS. 12A and 12B to move air into the preparation tube is a pincher that pinches the flexible tube, and can be moved across the tube with a knob 1260. A slot 1270 can be provided in the housing 1210 of the transfer device 1200 through which the knob 1260 and pincher 1250 could be moved by a user. As the pincher 1250 is moved towards the first internal section of the housing, it acts to push the volume Y of air up through the air transfer needle 1230 into the preparation tube above the serum 1285. Simultaneously, as the pincher is moved, a vacuum is created in the evacuated tube or eyedropper such that air from the evacuated tube is pulled into the flexible tubing 1240. FIG. 12B shows how the volume X of the serum 1285 can be moved into the evacuated tube 1290.

While a vent that extends through a slot of the housing could be beneficial in allowing a user to easily and properly position the vent needle as desired, such a vent could mistakenly be moved towards the preparation tube and cause the vent needle to puncture the preparation tube before the transfer needle has punctured the transfer tube. For various uses of transfer devices, especially where a device is to be a disposable, one-time use device, it would be advantageous to have all components of the device disposed within an outer housing to reduce or eliminate the risk of inadvertent adjustments.

Figure 13A:
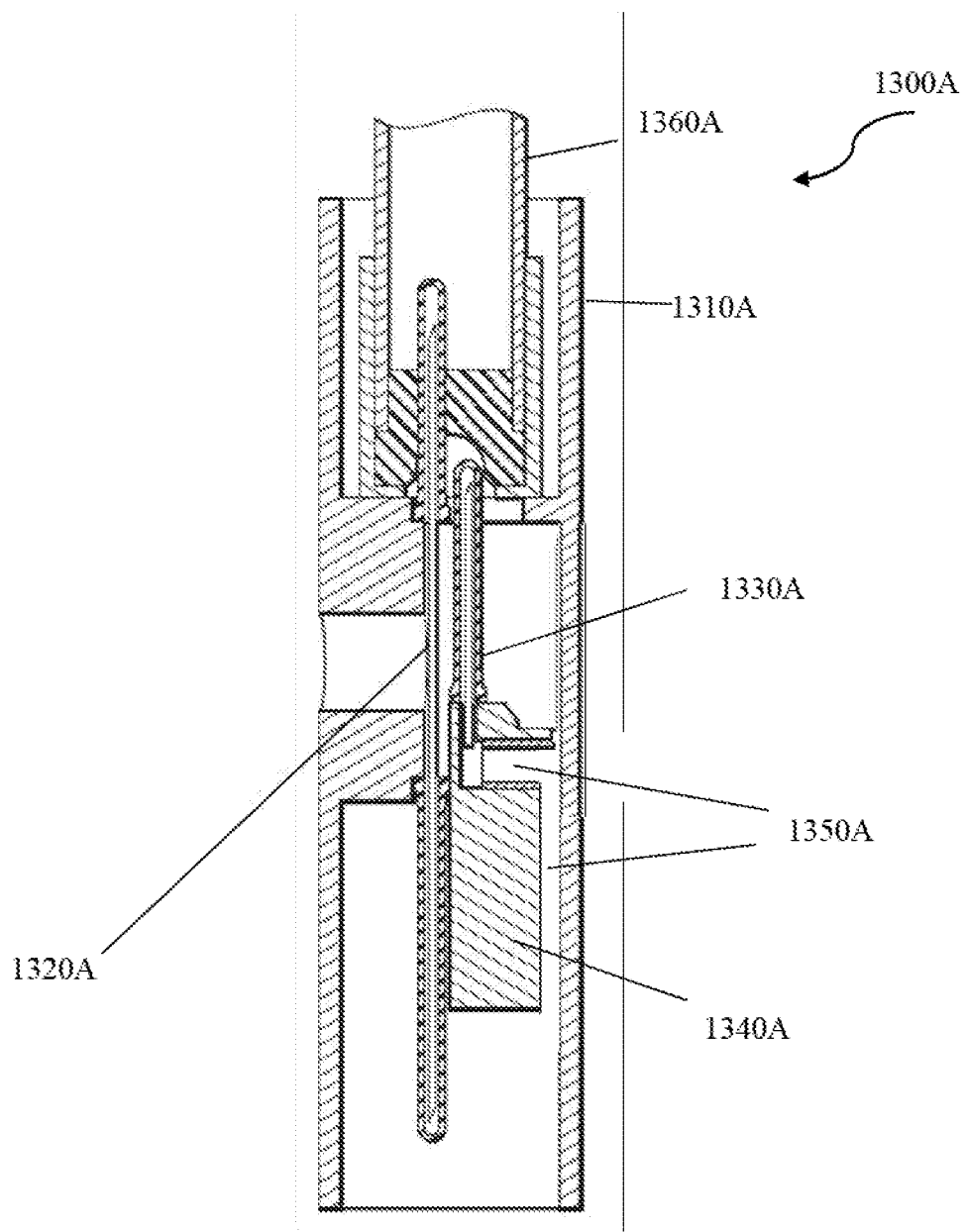
FIGS. 13A-C illustrate exemplary transfer devices having a vent that does not extend out of a housing.
Figure 13B:
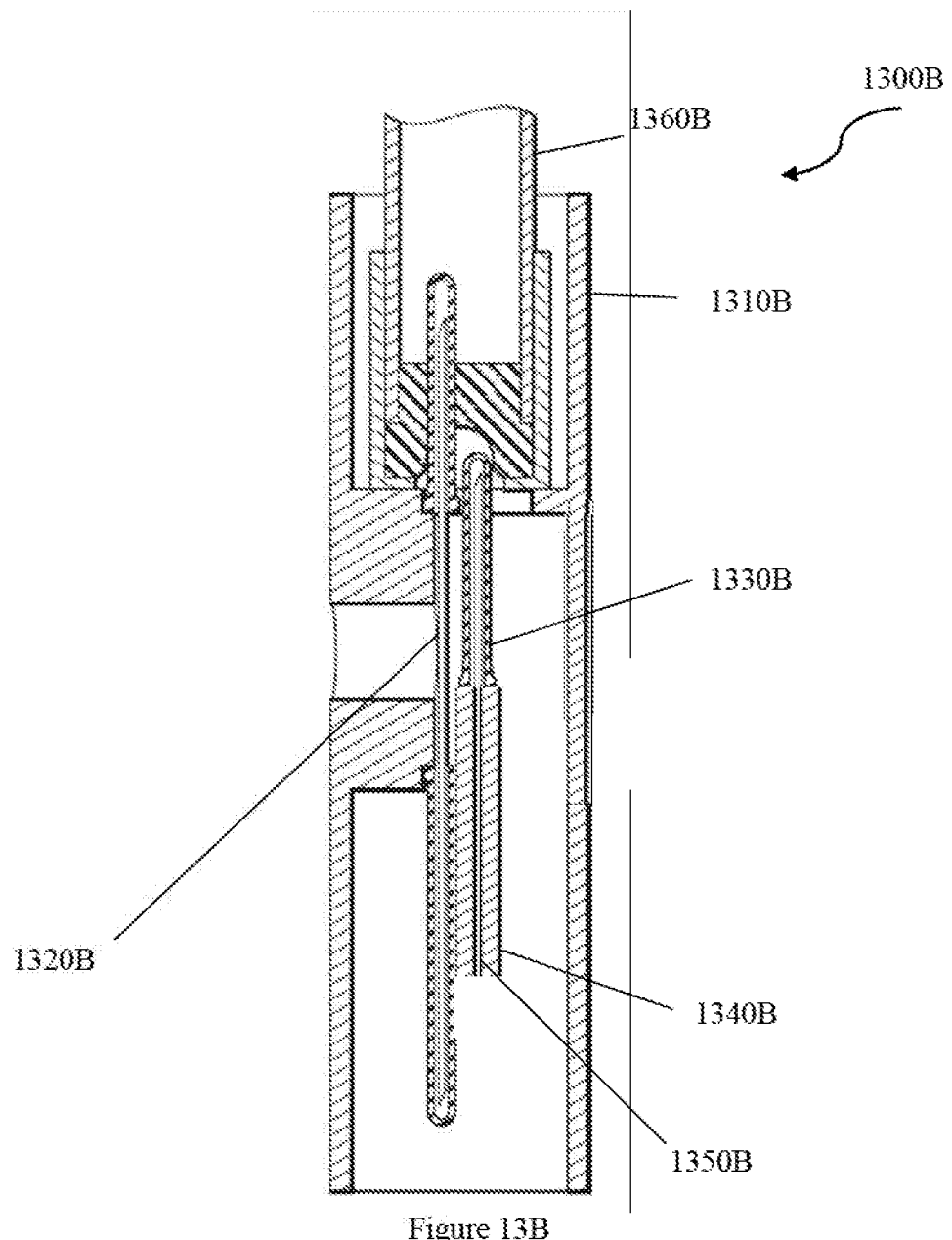
Figure 13C:
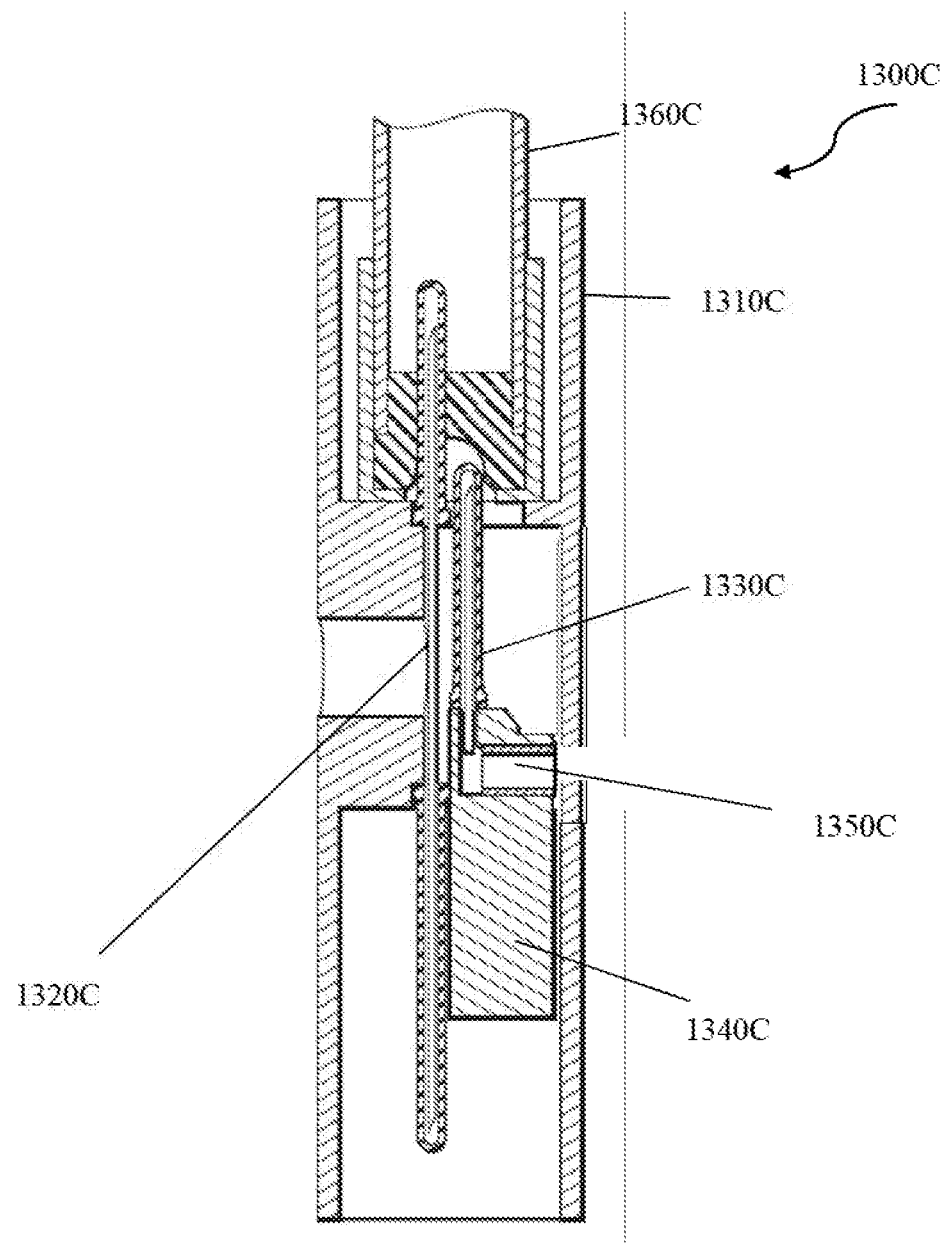

FIGS. 13A-C illustrate some exemplary transfer devices where all components are disposed within the housing, including a vent to allow for air flow into the preparation tube.

In FIG. 13A, transfer device 1300A includes a housing 1310A, which includes two open ends, and houses a transfer needle 1320A, a vent needle 1330A, a vent 1350A, a first base portion coupled with transfer needle 1320A, and a movable second base portion 1340A. As illustrated, no device component extends out from the housing wall. Instead, air can enter the vent, vent needle, and preparation tube 1360A via the second internal portion where a transfer tube would be placed.

In FIG. 13B, transfer device 1300B includes a housing 1310B, which includes two open ends, and houses a transfer needle 1320B, a vent needle 1330B, a vent 1350B, a first base portion coupled with transfer needle 1320B, and a movable second base portion 1340B, through which vent 1350B extends at least partially through in line with vent needle 1330B. It should be appreciated that base portion could comprise any suitable length to allow vent needle 1330B to be pushed into preparation tube 1360B to a desired point. It should also be appreciated that vent 1350B can extend through base portion 1340B at an angle, for example, towards the second internal portion and then extending out away from the transfer needle. As illustrated, no device component extends out from the housing wall. Instead, air can enter the vent, vent needle, and preparation tube 1360A via the second internal portion where a transfer tube would be placed.

In FIG. 13C, transfer device 1300C includes a housing 1310C, which includes two open ends, and houses a transfer needle 1320C, a vent needle 1330C, a vent 1350C, a first base portion coupled with transfer needle 1320C, and a movable second base portion 1340C. As illustrated, no device component extends out from the housing wall. Instead, air can enter the vent, vent needle, and preparation tube 1360C via an aperture in housing 1310C.

It should be appreciated that suitable transfer devices can have various configurations. Some preferred transfer devices include a transfer needle that is configured to simultaneously punctures a preparation tube and a transfer tube, and a vent needle that is movable to puncture the preparation tube, wherein the vent needle is coupled to a vent via which air could enter the preparation tube. The vent could be entirely disposed within a housing, or could extend out of the housing via a slot or other aperture.

Any of the transfer devices described herein can include one or more filters, which can be placed on or adjacent a vent, a vent needle, a transfer needle, a housing opening (e.g., an open end, a slot, or an aperture) or any other portion(s) of the device. Contemplated filters can at least one of (a) prevent leakage (e.g., when the device is tilted), and (b) sterilize air entering the device (e.g., vent, vent needle) or the preparation tube. In at least some embodiments, a filter can be hydrophobic. Where a sterile transfer is desirable, a filter for air sterility is especially preferred.

Figure 14:
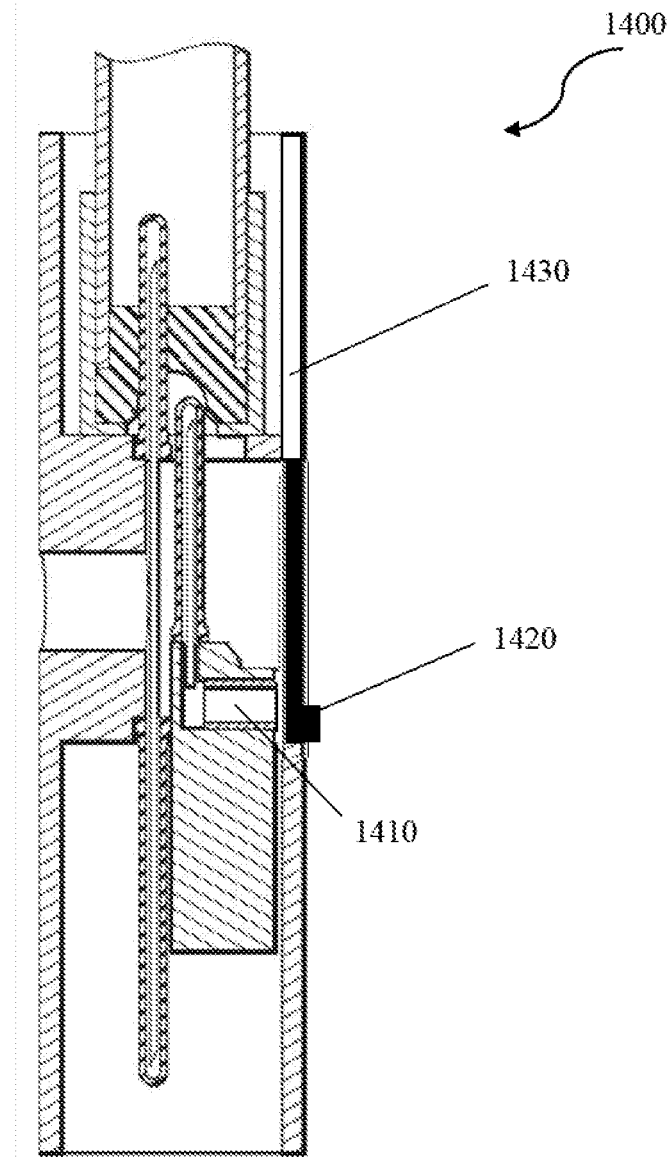
FIG. 14 illustrates a transfer device having a cover.

FIG. 14 illustrates transfer device 1400, which includes a cover that allows a user to access and move vent 1410 to a desired position. Cover 1420 includes a tab that allows a user to slide cover 1420 towards housing recess 1430. While cover 1420 is shown as a sliding door, it should be appreciated that any suitable movable cover is contemplated. Additionally or alternatively, cover 1420 could be fixed but transparent such that a user could view the position of vent 1410.

It should be appreciated that various other transfer devices are contemplated that would allow a fluid to be transferred from one sealed container to another. Typically, when a preparation tube is placed into one end of a commercially suitable transfer device, and the evacuation tube or eyedropper is placed into another end of the transfer device, a significant volume of fluid is not likely to move from the preparation tube into the evacuation tube via gravity alone. Although the evacuated tube is vacuum sealed and the system will naturally want to reach an equilibrium, the movement of the serum out of the preparation tube would create a vacuum in the preparation tube. These two vacuums would apparently work against each other and reach equilibrium before enough serum can pass into the evacuation tube. Therefore, it is advantageous to relieve the vacuum created in the preparation tube or to create a stronger vacuum in the evacuation tube. The above description illustrates some ways this could be achieved.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A transfer device, comprising:
a first needle, a second needle, and a base structure disposed within a housing;
wherein the housing has first and second open ends, and includes first and second internal sections on opposite ends of the base structure;
wherein the first needle is fixed to a first portion of the base structure, and includes a first end positioned within the first internal section of the housing, and a second end positioned within the second internal section of the housing;
wherein the second needle is coupled to a second portion of the base structure, and includes a first end positioned within the first internal section of the housing, and a second end that is coupled to a movable vent structure;
wherein the vent structure is fluidly coupled with the second internal section; and
wherein the second needle is movable from a first position to a second position such that a position of the first end relative to the first open end of the housing is adjustable.

2. The device of claim 1, wherein the second end is coupled to the vent structure at an angle.

3. The device of claim 1, wherein the second portion of the base structure is movable, and wherein the second needle is fixed to the second portion of the base structure.

4. The device of claim 1, wherein the vent structure is disposed entirely within the housing between the first and second open ends.

5. The device of claim 1, wherein at least one of the first and second open ends of the housing is covered by a membrane.

6. The transfer device of claim 1, further comprising one or more sleeves or coverings configured to cover an exposed needle portion to prevent contamination, provide sterility, or provide safety.

7. A transfer device, comprising:
a housing having a first internal section with a first open end, a second internal section with a second open end, and a base structure positioned between the first and second open ends;
wherein the base structure includes a first base portion fixedly coupled to an inner surface of the housing, and a second base portion movably coupled to the inner surface of the housing;
a first needle portion extending from the first base portion to the first internal section;
a second needle portion extending from the first base portion to the second internal section;
a third needle portion extending from the second base portion to the first internal section; and
a movable vent that extends through an elongated slot in a wall of the housing, and is coupled to the third needle portion.

8. The transfer device of claim 7, wherein the third needle portion is the only needle portion extending from the second base portion, and wherein the third needle portion does not extend to the second internal section.

9. A transfer device, comprising:
a housing having a first internal section, a second internal section, and a base structure positioned between the first and second open ends;
a first needle portion extending from the base structure to the first internal section;
a second needle portion extending from the base structure to the second internal section;
a third needle portion extending from the base structure to the first internal section;
a movable vent that is slidably coupled to an elongated slot in a wall of the housing; and
wherein the vent is fluidly coupled to the third needle portion.

10. A housing comprising:
a first internal section with a first open end, a second internal section with a second open end, and a base structure positioned between the first and second open ends;
wherein the base structure includes a first base portion fixedly coupled to an internal surface of the housing, and a second base portion movably coupled to the inner surface of the housing;
a first needle portion affixed to the first base portion and extending into both the first internal section in one direction and the second internal section in the other direction allowing liquid to flow through the first needle portion from a first container inserted into the first open end, into a second container inserted into the second open end;
a second needle portion extending from the second base portion to the first internal section; and
wherein the second base portion comprises a movable vent.

11. The housing as in claim 10, further comprising a vent that extends through a wall of the housing, or along the internal side of the housing, allowing air to vent through the second needle portion.

* * * * *